United States Patent
Odidi et al.

(10) Patent No.: US 10,632,205 B2
(45) Date of Patent: Apr. 28, 2020

(54) PHARMACEUTICAL COMPOSITION HAVING REDUCED ABUSE POTENTIAL

(71) Applicant: INTELLIPHARMACEUTICS CORP., Toronto (CA)

(72) Inventors: Isa Odidi, Toronto (CA); Amina Odidi, Toronto (CA)

(73) Assignee: INTELLIPHARMACEUTICS CORP, Toronto (CA)

( * ) Notice: Subject to any disclaimer, the term of this patent is extended or adjusted under 35 U.S.C. 154(b) by 0 days.

(21) Appl. No.: 14/724,865

(22) Filed: May 29, 2015

(65) Prior Publication Data

US 2015/0297734 A1 Oct. 22, 2015

Related U.S. Application Data

(63) Continuation of application No. 12/092,654, filed as application No. PCT/CA2007/000862 on May 14, 2007, now Pat. No. 9,078,827, which is a continuation-in-part of application No. 11/432,226, filed on May 12, 2006.

(51) Int. Cl.
| | |
|---|---|
| A61K 47/44 | (2017.01) |
| A61K 47/02 | (2006.01) |
| A61K 9/48 | (2006.01) |
| A61K 31/485 | (2006.01) |
| A61K 9/06 | (2006.01) |
| A61K 31/137 | (2006.01) |

(52) U.S. Cl.
CPC ............. *A61K 47/44* (2013.01); *A61K 9/06* (2013.01); *A61K 9/485* (2013.01); *A61K 9/4825* (2013.01); *A61K 9/4858* (2013.01); *A61K 9/4866* (2013.01); *A61K 9/4875* (2013.01); *A61K 9/4891* (2013.01); *A61K 31/137* (2013.01); *A61K 31/485* (2013.01); *A61K 47/02* (2013.01); *A61K 9/4808* (2013.01)

(58) Field of Classification Search
CPC .................. A61K 31/485; A61K 9/4875
See application file for complete search history.

(56) References Cited

U.S. PATENT DOCUMENTS

| | | |
|---|---|---|
| 2,540,979 A | 2/1951 | MacDonnell |
| 3,254,088 A | 5/1966 | Juda et al. |
| 3,493,657 A | 2/1970 | Lewenstein |
| 3,629,393 A | 12/1971 | Nakamoto et al. |
| 3,728,445 A | 4/1973 | Bardani |
| 3,773,955 A | 11/1973 | Pachter |
| 3,789,117 A | 1/1974 | Tsujino |
| 3,819,706 A | 6/1974 | Mehta |
| 3,845,770 A | 11/1974 | Higuchi |
| 3,856,721 A | 12/1974 | Fritschel |
| 3,916,899 A | 11/1975 | Theeuwes et al. |
| 4,008,719 A | 2/1977 | Theeuwes |
| 4,016,880 A | 4/1977 | Theeuwes |
| 4,034,758 A | 7/1977 | Theeuwes |
| 4,036,228 A | 7/1977 | Theeuwes |
| 4,045,563 A | 8/1977 | Berntsson et al. |
| 4,060,598 A | 11/1977 | Groppenbacher et al. |
| 4,077,407 A | 3/1978 | Theeuwes |
| 4,160,452 A | 7/1979 | Theeuwes |
| 4,161,477 A | 7/1979 | Long |
| 4,183,838 A | 1/1980 | Gagliani |
| 4,183,839 A | 1/1980 | Gagliani |
| 4,193,985 A | 3/1980 | Bechgaard |
| 4,200,098 A | 4/1980 | Ayer |
| 4,218,433 A | 8/1980 | Kooichi et al. |
| 4,248,856 A | 2/1981 | Guley et al. |
| 4,250,136 A | 2/1981 | Rex |
| 4,252,786 A | 2/1981 | Weiss et al. |
| 4,255,431 A | 3/1981 | Junggren et al. |
| 4,309,405 A | 1/1982 | Guley et al. |
| 4,327,725 A | 5/1982 | Cortese |
| 4,330,338 A | 5/1982 | Banker |
| 4,337,257 A | 6/1982 | Junggren |
| 4,389,393 A | 6/1983 | Schor et al. |
| 4,425,441 A | 1/1984 | Gagliani et al. |
| 4,457,933 A | 7/1984 | Gordon |
| 4,461,759 A | 7/1984 | Dunn |
| 4,486,412 A | 12/1984 | Shah et al. |

(Continued)

FOREIGN PATENT DOCUMENTS

| | | |
|---|---|---|
| CA | 2286684 | 10/1998 |
| CA | 2529984 | 12/2004 |

(Continued)

OTHER PUBLICATIONS

Buhse, Lucinda, et al. "Topical drug classification." International journal of pharmaceutics 295.1-2 (2005): 101-112.*

(Continued)

*Primary Examiner* — Bethany P Barham
*Assistant Examiner* — Peter Anthopolos
(74) *Attorney, Agent, or Firm* — Thomas | Horstemeyer, LLP

(57) ABSTRACT

A pharmaceutical paste composition comprising an active ingredient such as an addictive substance, a controlled release agent, and a pharmaceutically suitable aqueous or non-aqueous carrier. The composition may comprise one or more of a clay, or an oily, waxy, or fatty substance. The composition may be filled into a capsule or other dispensing device. The composition may reduce dose dumping of an active ingredient. Methods of making and using the composition are also described.

12 Claims, 1 Drawing Sheet

(56) References Cited

U.S. PATENT DOCUMENTS

| | | | |
|---|---|---|---|
| 4,508,905 A | 4/1985 | Junggren | |
| 4,514,538 A | 4/1985 | Shvakhman et al. | |
| 4,517,112 A | 5/1985 | Mardis et al. | |
| 4,518,717 A | 5/1985 | Long et al. | |
| 4,545,412 A | 10/1985 | Gamberini | |
| 4,582,835 A | 4/1986 | Lewis | |
| 4,606,909 A | 8/1986 | Bechgaard | |
| 4,610,870 A | 9/1986 | Jain et al. | |
| 4,612,008 A | 9/1986 | Wong et al. | |
| 4,626,539 A * | 12/1986 | Aungst | A61K 9/0014 514/282 |
| 4,628,098 A | 12/1986 | Nohara et al. | |
| 4,666,705 A | 5/1987 | DeCrosta et al. | |
| 4,676,929 A | 6/1987 | Rittler | |
| 4,684,516 A | 8/1987 | Bhutani | |
| 4,686,230 A | 8/1987 | Rainer et al. | |
| 4,689,333 A | 8/1987 | Nohara et al. | |
| 4,704,285 A | 11/1987 | Alderman | |
| 4,708,834 A | 11/1987 | Cohen et al. | |
| 4,713,248 A | 12/1987 | Kjornaes et al. | |
| 4,728,512 A | 3/1988 | Mehta | |
| 4,756,911 A | 7/1988 | Drost et al. | |
| 4,758,579 A | 7/1988 | Kohl et al. | |
| 4,765,989 A | 8/1988 | Wong et al. | |
| 4,783,337 A | 11/1988 | Wong et al. | |
| 4,786,505 A | 11/1988 | Lovgren et al. | |
| 4,812,446 A | 3/1989 | Brand | |
| 4,818,760 A | 4/1989 | Binder et al. | |
| 4,832,958 A | 5/1989 | Baudier et al. | |
| 4,844,905 A | 7/1989 | Ichikawa et al. | |
| 4,844,909 A * | 7/1989 | Goldie | A61K 9/1652 424/480 |
| 4,845,118 A | 7/1989 | Lang et al. | |
| 4,851,228 A | 7/1989 | Zentner et al. | |
| 4,853,230 A | 8/1989 | Lovgren et al. | |
| 4,869,908 A | 9/1989 | Kirschner et al. | |
| 4,880,631 A | 11/1989 | Haslam | |
| 4,886,668 A | 12/1989 | Haslam | |
| 4,891,223 A | 1/1990 | Ambegaonkar et al. | |
| 4,892,742 A | 1/1990 | Shah | |
| 4,900,557 A | 2/1990 | Dell et al. | |
| 4,904,476 A | 2/1990 | Mehta et al. | |
| 4,927,640 A | 5/1990 | Dahlinder et al. | |
| 4,935,243 A | 6/1990 | Borkan et al. | |
| 4,940,587 A | 7/1990 | Jenkins et al. | |
| 4,940,588 A | 7/1990 | Sparks et al. | |
| 4,946,853 A | 8/1990 | Bannon et al. | |
| 4,963,365 A | 10/1990 | Samejima et al. | |
| 4,965,269 A | 10/1990 | Brandstrom et al. | |
| 4,966,768 A | 10/1990 | Michelucci et al. | |
| 5,000,962 A | 3/1991 | Sangekar et al. | |
| 5,004,614 A | 4/1991 | Staniforth | |
| 5,021,433 A | 6/1991 | Alminger et al. | |
| 5,028,434 A | 7/1991 | Barclay et al. | |
| 5,045,552 A | 9/1991 | Souda et al. | |
| 5,049,394 A | 9/1991 | Howard et al. | |
| 5,071,643 A | 12/1991 | Yu et al. | |
| 5,073,384 A | 12/1991 | Valentine et al. | |
| 5,077,051 A | 12/1991 | Gallopo | |
| 5,123,146 A | 6/1992 | Olson | |
| 5,149,538 A | 9/1992 | Granger et al. | |
| 5,149,702 A | 9/1992 | Yamada et al. | |
| 5,190,763 A | 3/1993 | Edgren et al. | |
| 5,202,128 A | 4/1993 | Morella et al. | |
| 5,219,572 A | 6/1993 | Sivaramakrishna | |
| 5,229,131 A | 7/1993 | Amidon et al. | |
| 5,236,714 A | 8/1993 | Lee et al. | |
| 5,240,712 A | 8/1993 | Smith | |
| 5,252,339 A | 10/1993 | Cristofori et al. | |
| 5,260,069 A | 11/1993 | Chen | |
| 5,286,497 A | 2/1994 | Hendrickson et al. | |
| 5,288,500 A | 2/1994 | Ibsen | |
| 5,290,816 A | 3/1994 | Blumberg | |
| 5,300,291 A * | 4/1994 | Sablotsky | A61F 13/0276 424/448 |
| 5,330,766 A | 7/1994 | Morella et al. | |
| 5,376,388 A | 12/1994 | Meyers | |
| 5,378,474 A | 1/1995 | Morella et al. | |
| 5,393,528 A | 2/1995 | Staab | |
| 5,415,871 A | 5/1995 | Pankhania et al. | |
| 5,425,950 A | 6/1995 | Dandiker et al. | |
| 5,430,042 A | 7/1995 | Lindberg et al. | |
| 5,445,829 A | 8/1995 | Paradissis et al. | |
| 5,458,887 A | 10/1995 | Chen et al. | |
| 5,472,711 A | 12/1995 | Baichwal | |
| 5,480,335 A | 1/1996 | Caveza | |
| 5,503,846 A | 4/1996 | Wehling | |
| 5,508,040 A | 4/1996 | Chen | |
| 5,527,545 A | 6/1996 | Santus et al. | |
| 5,595,762 A | 1/1997 | Derrieu | |
| 5,681,581 A | 10/1997 | Dunn | |
| 5,681,585 A | 10/1997 | Oshlack | |
| 5,708,017 A | 1/1998 | Dave et al. | |
| 5,713,000 A | 1/1998 | Larson | |
| 5,736,159 A | 4/1998 | Chen et al. | |
| 5,753,265 A | 5/1998 | Bergstrand | |
| 5,759,577 A | 6/1998 | Barcomb | |
| 5,760,121 A | 6/1998 | Beall et al. | |
| 5,780,055 A | 7/1998 | Habib et al. | |
| 5,783,215 A | 7/1998 | Arwidsson et al. | |
| 5,795,583 A | 8/1998 | Grune et al. | |
| 5,800,422 A | 9/1998 | Dong et al. | |
| 5,817,338 A | 10/1998 | Bergstrand | |
| 5,840,329 A | 11/1998 | Bai | |
| 5,840,910 A | 11/1998 | Souda et al. | |
| 5,879,708 A | 3/1999 | Makino et al. | |
| 5,955,106 A | 9/1999 | Moeckel et al. | |
| 5,972,329 A | 10/1999 | Chuang et al. | |
| 5,998,445 A | 12/1999 | Souda et al. | |
| 6,022,562 A | 2/2000 | Autant et al. | |
| 6,039,975 A | 3/2000 | Shah et al. | |
| 6,046,177 A | 4/2000 | Stella et al. | |
| 6,068,853 A | 5/2000 | Giannos et al. | |
| 6,090,401 A | 7/2000 | Gowan et al. | |
| 6,099,859 A | 8/2000 | Cheng et al. | |
| 6,106,864 A | 8/2000 | Dolan et al. | |
| 6,183,776 B1 | 2/2001 | Depui et al. | |
| 6,183,777 B1 | 2/2001 | Chen et al. | |
| 6,194,001 B1 | 2/2001 | Gribbon et al. | |
| 6,210,710 B1 | 4/2001 | Skinner | |
| 6,228,400 B1 | 5/2001 | Lee et al. | |
| 6,251,432 B1 | 6/2001 | Mazer et al. | |
| 6,261,582 B1 | 7/2001 | Needham et al. | |
| 6,270,804 B1 | 8/2001 | Getz et al. | |
| 6,296,876 B1 | 10/2001 | Odidi et al. | |
| 6,312,723 B1 | 11/2001 | Whittle et al. | |
| 6,312,724 B1 | 11/2001 | Odidi et al. | |
| 6,368,635 B1 | 4/2002 | Akiyama et al. | |
| 6,433,040 B1 | 8/2002 | Dellamary et al. | |
| 6,479,075 B1 | 11/2002 | Odidi et al. | |
| 6,489,346 B1 | 12/2002 | Phillips | |
| 6,491,949 B2 | 12/2002 | Faour et al. | |
| 6,509,037 B2 | 1/2003 | Odidi | |
| 6,527,051 B1 | 3/2003 | Reddy et al. | |
| 6,555,127 B2 | 4/2003 | Steiner | |
| 6,558,704 B1 | 5/2003 | Bartholomaeus | |
| 6,569,453 B2 | 5/2003 | Linder et al. | |
| 6,599,529 B1 | 7/2003 | Skinhoj | |
| 6,605,300 B1 | 8/2003 | Burnside et al. | |
| 6,607,751 B1 * | 8/2003 | Odidi | A61K 9/1611 424/468 |
| 6,627,635 B2 | 9/2003 | Palermo et al. | |
| 6,645,524 B2 | 11/2003 | Midha et al. | |
| 6,645,528 B1 | 11/2003 | Straub et al. | |
| 6,645,988 B2 | 11/2003 | Phillips | |
| 6,652,882 B1 | 11/2003 | Odidi et al. | |
| 6,673,367 B1 | 1/2004 | Goldenheim et al. | |
| 6,676,966 B1 | 1/2004 | Odidi et al. | |
| 6,696,088 B2 | 2/2004 | Oshlack et al. | |
| 6,699,885 B2 | 3/2004 | Phillips | |
| 6,780,882 B2 | 8/2004 | Phillips | |
| 6,800,668 B1 | 10/2004 | Odidi et al. | |
| 6,902,742 B2 | 6/2005 | Devane et al. | |
| 6,911,217 B1 | 6/2005 | Gren et al. | |

(56) References Cited

U.S. PATENT DOCUMENTS

| | | |
|---|---|---|
| 6,946,146 B2 | 9/2005 | Mulye |
| 6,991,804 B2 | 1/2006 | Helmus et al. |
| 7,090,867 B2 | 8/2006 | Odidi et al. |
| 7,135,465 B2 | 11/2006 | Abramowitz et al. |
| 7,157,103 B2 | 1/2007 | Sackler |
| 7,858,119 B1 | 12/2010 | Odidi et al. |
| 7,906,143 B1 | 3/2011 | Odidi et al. |
| 9,078,827 B2 * | 7/2015 | Odidi .................. A61K 9/06 |
| 2001/0006649 A1 | 7/2001 | Chen |
| 2002/0002147 A1 | 1/2002 | Abramowitz et al. |
| 2002/0045646 A1 | 4/2002 | Phillips |
| 2002/0086885 A1 | 7/2002 | Odaka et al. |
| 2002/0110590 A1 | 8/2002 | Shaked et al. |
| 2002/0128293 A1 | 9/2002 | Rampal et al. |
| 2002/0132005 A1 | 9/2002 | Faour |
| 2002/0150535 A1 | 10/2002 | Madras et al. |
| 2003/0064099 A1 | 4/2003 | Oshlack et al. |
| 2003/0064101 A1 | 4/2003 | Mehta et al. |
| 2003/0068370 A1 * | 4/2003 | Sackler .............. A61K 9/1611 424/465 |
| 2003/0068371 A1 | 4/2003 | Oshlack et al. |
| 2003/0077297 A1 | 4/2003 | Chen et al. |
| 2003/0118641 A1 | 6/2003 | Maloney et al. |
| 2003/0118669 A1 | 6/2003 | Phillips |
| 2003/0185887 A1 | 10/2003 | Chen et al. |
| 2003/0215507 A1 | 11/2003 | Sherman et al. |
| 2003/0215527 A1 | 11/2003 | Phillips |
| 2003/0220413 A1 | 11/2003 | Petereit et al. |
| 2003/0235616 A1 | 12/2003 | Sowden et al. |
| 2004/0048896 A1 | 3/2004 | Phillips |
| 2004/0058018 A1 | 3/2004 | Phillips |
| 2004/0101558 A1 | 5/2004 | Dietrich et al. |
| 2004/0131669 A1 | 7/2004 | Kerc |
| 2004/0171646 A1 | 9/2004 | Phillips |
| 2004/0185093 A1 | 9/2004 | Szymczak |
| 2004/0198775 A1 | 10/2004 | Fraser et al. |
| 2004/0265370 A1 | 12/2004 | Odidi et al. |
| 2004/0265380 A1 | 12/2004 | Delmas et al. |
| 2005/0004171 A1 | 1/2005 | Phillips |
| 2005/0042304 A1 | 2/2005 | Phillips |
| 2005/0054682 A1 | 3/2005 | Phillips |
| 2005/0129778 A1 | 6/2005 | Mulye |
| 2005/0186268 A1 | 8/2005 | Hoshi et al. |
| 2005/0196436 A1 | 9/2005 | Chantranukul et al. |
| 2005/0214373 A1 | 9/2005 | Desai et al. |
| 2006/0003001 A1 | 1/2006 | Devane et al. |
| 2006/0004193 A1 | 1/2006 | Muller |
| 2006/0018948 A1 | 1/2006 | Guire et al. |
| 2006/0024361 A1 | 2/2006 | Odidi et al. |
| 2006/0039864 A1 | 2/2006 | Bartholomaus et al. |
| 2006/0039976 A1 | 2/2006 | Odidi et al. |
| 2006/0099246 A1 | 5/2006 | Tanner et al. |
| 2006/0017336 A1 | 6/2006 | Knauff |
| 2006/0115527 A1 | 6/2006 | Hassan et al. |
| 2006/0153909 A1 | 7/2006 | Motoune |
| 2006/0205681 A1 | 9/2006 | Moaddeb |
| 2007/0003619 A1 | 1/2007 | Smith |
| 2007/0009589 A1 | 1/2007 | Raghupathi et al. |
| 2007/0077293 A1 | 4/2007 | Park |
| 2007/0104778 A1 | 5/2007 | Zeng et al. |
| 2007/0131357 A1 | 6/2007 | Wu |
| 2007/0166370 A1 | 7/2007 | Odidi et al. |
| 2007/0286902 A1 | 12/2007 | Xie et al. |
| 2009/0082466 A1 | 3/2009 | Babul |
| 2009/0220613 A1 | 9/2009 | Odidi et al. |

FOREIGN PATENT DOCUMENTS

| | | |
|---|---|---|
| CA | 2551946 | 7/2005 |
| CN | 1634116 | 7/2005 |
| DE | 1204363 | 8/1964 |
| DE | 3531487 | 8/1985 |
| DE | 3943242 | 6/1990 |
| DE | 19635676 | 3/1998 |
| EP | 0005129 | 4/1981 |
| EP | 0157695 | 9/1985 |
| EP | 0166287 | 1/1986 |
| EP | 0174726 | 3/1986 |
| EP | 0184322 | 6/1986 |
| EP | 0234485 | 9/1987 |
| EP | 080341 | 10/1987 |
| EP | 0261478 | 3/1988 |
| EP | 0268956 | 6/1988 |
| EP | 0270305 | 6/1988 |
| EP | 0342522 | 11/1989 |
| EP | 0366321 | 5/1990 |
| EP | 0403383 | 12/1990 |
| EP | 0434999 | 7/1991 |
| EP | 0453001 | 10/1991 |
| EP | 0527638 | 2/1993 |
| EP | 0533790 | 3/1993 |
| EP | 0797991 | 10/1997 |
| EP | 960620 | 12/1999 |
| EP | 1017370 | 7/2000 |
| EP | 1493435 | 1/2005 |
| EP | 1731142 | 12/2006 |
| FR | 2419722 | 1/1979 |
| FR | 2624012 | 6/1989 |
| FR | 2778848 | 11/1999 |
| GB | 2134516 | 8/1984 |
| GB | 2163747 | 3/1986 |
| HU | 203477 | 1/1991 |
| JP | 2002068964 | 3/2002 |
| JP | 2005500364 | 1/2005 |
| JP | 2005508359 | 3/2005 |
| JP | 2005515153 | 5/2005 |
| WO | 8503436 | 8/1985 |
| WO | 8705212 | 9/1987 |
| WO | 9011070 | 10/1990 |
| WO | 09107950 | 6/1991 |
| WO | 09116885 | 11/1991 |
| WO | 9119710 | 12/1991 |
| WO | 932377 | 8/1993 |
| WO | 9428882 | 12/1994 |
| WO | 9816206 | 4/1998 |
| WO | 9851287 | 11/1998 |
| WO | 09912524 | 3/1999 |
| WO | 0230398 | 4/2002 |
| WO | 03013475 | 2/2003 |
| WO | 03013538 | 2/2003 |
| WO | 2003013476 | 2/2003 |
| WO | 03009846 | 6/2003 |
| WO | 03086364 | 10/2003 |
| WO | 04000825 | 12/2003 |
| WO | 2004002418 | 1/2004 |
| WO | 2004024128 | 3/2004 |
| WO | 200405002 | 6/2004 |
| WO | 04056354 | 8/2004 |
| WO | 2005032474 | 1/2005 |
| WO | 0137817 | 3/2005 |
| WO | 2005021009 | 3/2005 |
| WO | 2005065661 | 7/2005 |
| WO | 2005097075 | 10/2005 |
| WO | 2005099674 | 10/2005 |
| WO | 2006011592 | 2/2006 |
| WO | 2006017336 | 2/2006 |
| WO | 2006085335 | 8/2006 |
| WO | 2007082770 | 7/2007 |
| WO | 2008122993 | 10/2008 |
| WO | 2009113061 | 9/2009 |
| WO | 2010044842 | 4/2010 |
| WO | 2012002644 | 1/2012 |

OTHER PUBLICATIONS

Zulfiker, Abu Hasanat Md, et al. "Formulation Development Using Maize Starch & Avicel PH101 as Disintegrating Agents and Their Effect on Physical Characteristics & In Vitro Release Profile." International Journal of Pharmaceutical Sciences and Research 2.8 (2011): 2136.*

Remington: The Science and Practice of Pharmacy. 21st edition (2005) pp. 802-803 and 1071-1072.

(56) References Cited

OTHER PUBLICATIONS

U.S. Appl. No. 10/561,700 Published on Jul. 19, 2007.
Odidi, Non-Final Office Action dated Mar. 12, 2010 for U.S. Appl. No. 11/432,226, filed May 12, 2006. (Copy not provided as PTO generated.).
U.S. Appl. No. 12/696,118 Published on May 27, 2010.
Odidi, Non-Final Office Action dated Jun. 25, 2009 for U.S. Appl. No. 11/432,226, filed May 12, 2006. (Copy not provided as PTO generated.).
Odidi, International Search Report and Written Opinion dated Aug. 31, 2007 for PCT/CA2007/000862 filed May 14, 2007.
Odidi, International Preliminary Report on Patentability dated Nov. 27, 2008 for PCT/CA2007/000862 filed May 14, 2007.
Office Action dated Nov. 25, 2009 for Canadian Patent Application No. 2,626,558 filed Jan. 2006.
Torpac, Capsul Size Chart, 2000, pp. 1-3.
Paste, http://www.thefreedictionary.com/paste,accessed Jun. 29, 2012.
Supplemental European Search Report Prepared by Miralles J. Gimenez dated Aug. 23, 2012.
Supplemental European Search Report Prepared by Antonio Raposo dated Aug. 2, 2012.
Anderson, M. et al., Analysis of Film Coating Thickness and Surface Area of Pharmaceutical Pellets using Fluorescence Microscopy and Image Analysis, J. Pharmaceutical and Biomedical Analysis, (2000), vol. 22, pp. 325-339.
Arora, S. et al, Pulsatie Drug Delivery Systems: An Approach for Controlled Drug Delivery, Indian J. Pharm. Sci., (2006), vol. 68, pp. 295-300.
Pharmaceutics: The science of dosage form design. Ed. Michael E. Aulton. London: Churchill Livingstone, 1988, pp. 316-321.
Aulton, M. E.—The science of dosage form design, (1988), pp. 316-321, (Churchill Livingstone Ed.), Pharmaceutics.
Banga, A. et al., "Incorporation of Simethicone into Syrup or Clear Base Liquid Orals", Drug Development and Industrial Pharmacy, (1989), vol. 15(5), pp. 671-704.
Conner, A. L. et al., A Scintigraphic Study to Investigate the Potential for Altered Gut Distribution of Loperaminde from a Loperaminde-Simethicone Formation in Man, European Journal of Pharmaceutical Sciences, (2001), vol. 13, pp. 369-374.
Dashevsky, A. etal., pH-independent Release of Baisc Drug from Pellets Coated with the Extended Release Polymer Dispersion Kollicoat.RTM. SR 30 D and the Enteric Polymer Dispersion Kollicoat.RTM. MAE 30 DP, European Journal of Pharmaceutics and Biopharmaceuticals, (2004), vol. 58, pp. 45-49 (available online Jun. 1, 2004).
Deshpande, A. et al., Development of a Novel Controlled-Release System for Gastric Retention, Pharmaceutical Research, (1997), vol. 14, No. 6, pp. 815-819.
Krogel, I. et al., Floating of Pulsatile Drug Delivery Systems Based on Coated Efferescent Cores, International Journal of Pharmaceutics, (1999) vol. 187, pp. 175-184 anl.
Laizure, S. C. et al., Stability of Bupropion and its Major Metabolites in Human Plasma, Therapeutic Drug Monitoring (1985), vol. 7 (4); p. 447.
Lehmann, K. et al.,—Fast Disintegrating Controlled Release Tablets from Coated Particles—Drugs Made in Germany, (1994) vol. 37, No. 2, pp. 53-60.
Martindale, The Extra Pharmacopoeia, 30th Ed. (The Pharmaceutical Press, London 1993).
Rakur, G. et al., 2-((2-Pyridylm-ethyl) Sulfiny) Benzimidazoles: Acid Sensitive Suicide Inhibitors of the Proton Transport System in the Parietal Cell, Biochem Biophys. Res. Comm. (1985), vol. 128, No. 1, pp. 477-484.
Remington's Pharmaceutical Sciences, 18th ed, (1990), Chapter 83, pp. 1539-1540.
Sathe, P.M. et al, Drug Product Performance, In Vitro, Generic Drug Product Development, (2004), vol. 143, Chapter 3, pp. 187-209.
Steward, P.A. Review of Pharmaceutical Controlled Release Method and Devices, (1995) 12 pages.
Sungthongjeen, S. et al.,—Development of Pulsatile Release Tablets with Swelling and Rupturable Layers, Journal of Controlled Release, (2004), vol. 95, pp. 1147-1159.
Sunshine, et al., "Analgesic Efficacy of Pentazocine Versus a Pentazocine-Naxloxone Combination Following Oral Administration", Clin. J. Pain, (1988), vol. 4, pp. 35-40.
Venkatraman et al., Chapter 22, An overview of Controlled Release Systems, Handbook of Pharmaceutical Controlled release Technology by Donald Wise, Published, (2002) p. 443.
Walters, S. M., Influence of pH on Hydrolytic Decomposition of Dimethylpropion Hydrochloride: Stability Studies on Drug Substance and Tables using High-Performance Liquid Chromatograph, J. Pharma Science, (1980), vol. 69 (10), p. 1208.
Wang, R. et al., Crossover and Parallel Study of Oral Analgesics, J. Clin. Pharmacl., (1981) Vo. 21, pp. 162-168.
Merriam-Webster Online Dictionary, http://www.meriam-webster.com/dictionary/prevent, obtained online Feb. 18, 2008.
Merriam-Webster Online Dictionary, http://www.meriam-webster.com/dictionary/cure, obtained online Dec. 16, 2009.
U.S. Appl. No. 12/225,956 Published on Dec. 10, 2009.
European Patent Application No. 04 737 76.2-2112, Examination Report dated Nov. 18, 2009.
Office Action for U.S. Appl. No. 10/561,700 dated Dec. 27, 2007.
Office Action for U.S. Appl. No. 10/561,700 dated Mar. 18, 2008.
Office Action for U.S. Appl. No. 10/561,700 dated Apr. 17, 2009.
Office Action for U.S. Appl. No. 10/561,700 dated Sep. 3, 2009.
Office Action for U.S. Appl. No. 10/861,809 dated Sep. 28, 2009.
Office Action for U.S. Appl. No. 10/861,809 dated Nov. 26, 2008.
Office Action for U.S. Appl. No. 10/861,809 dated Nov. 13, 2007.
Office Action for U.S. Appl. No. 12/092,654 dated Mar. 12, 2010.
U.S. Appl. No. 11/473,386 Published on Mar. 22, 2007.
U.S. Appl. No. 09/947,464 Published on Mar. 13, 2003.
U.S. Appl. No. 12/225,954 Published on Sep. 3, 2009.
U.S. Appl. No. 11/432,226, filed May 12, 2006, Pending since 2006 yet unpublished.
U.S. Appl. No. 12/092,654 Published on Sep. 17, 2009.
U.S. Appl. No. 10/924,649 Published on Feb. 23, 2006.
U.S. Appl. No. 10/900,415 Published on Feb. 2, 2006.
U.S. Appl. No. 10/880,474 Published on Jan. 5, 2006.
U.S. Appl. No. 11/315,868, filed Dec. 23, 2005, Pending since 2005 yet unpublished.
U.S. Appl. No. 11/315,868 Pending since 2005 yet unpublished filed Dec. 23, 2005.
Paste, www.thefreedictionary.com/paste, accessed Jun. 26, 2012.
International Search Report from PCT/CA2013/000610; dated Sep. 18, 2013; Prepared by Nasreddine Slougui on Sep. 13, 2013.
Super Disintegrants: Characterization and Function, 2007 by Informa Healthcare USA, Inc., 18 pages.
Ganesh Rasve, et al.; Pulsatile Drug Delivery System: Current Scenario; International Journal of Pharma and Bio Sciences; vol. 2 / Issue 3/ Jul.-Sep. 2011; 12 pages.
International Search Report and Written Opinion; PCT/CA2007/000540 (dated Jul. 23, 2007).
International Search Report and Written Opinion; PCT/CA2007/000548 (dated Jul. 27, 2007).
International Search Report and Written Opinion; PCTCA2007/000550 (dated Jul. 23, 2007).
International Search Report and Written Opinion; PCT/CA2007/000862 (dated Aug. 31, 2007).
International Preliminary Report on Patentability dated Nov. 27, 2008; PCT/CA2007/000862.
International Preliminary Examination Report; PCT/CA2002/01360 (dated Feb. 2, 2002).
International Search Report; PCT/CA2002/00054 published Oct. 17, 2002).
International Search Report and Written Opinion; PCT/CA2004/000825 (dated Oct. 22, 2004).
Encyclopaedia of Polymer Science and Technology; vol. 10 (1969); published by John Wiley & Sons.
Iinternational Search Report and Written Opinion including references U.S. Pub. 2007/0104778 and 2006/0039864; U.S. Pat. Nos. 6,607,751 and 6,627,635.

(56) References Cited

OTHER PUBLICATIONS

Sunshine, et al.; Analgesic Efficacy of Pentazocine Versus a Pentazocine-Naxioxone Combination Following Oral Administration, Clin. J. Pain, 1988: 4:35-40.
Wang et al.; Crossover and Parallel Study of Oral Analgesics; J. Clin. Pharmacl., 1981; 21:162-8.
Remington's Pharmaceutical Sciences, 18.sup.th ed. Chapter 83, pp. 1539-1540 (1990).
A. Banga et al.; Incorporation of Simethicone into Syrup or Clear Base Liquid Orals; Drug Development and Industrial Pharmacy; 15(5), pp. 671-704; 1998.
Merriam-Webster Dictionary; definition of "Paste"; 1 page, accessed Dec. 16, 2014.
Canadian Examination Search Report, 50 rue Victoria, Place du Portage 1, Gatineau Quebec K1A OC9; dated Sep. 29, 2017 4 pages, U.S. Pat. No. 2,648,278.
European Patent Search Report; dated Jul. 6, 2018; Application No. 07719784.6-1114; European Patent Office, Munich, Germany; 6 pages.
Porro et al., "Efficacy of pantoprazole in the prevention of peptic ulcers, induced by non-steroidal anti-inflammatory drugs: a prospective, placebo-controlled, double-blind, parallel-group study", Digest Liver Dis 2000; 32: 201-208.

\* cited by examiner

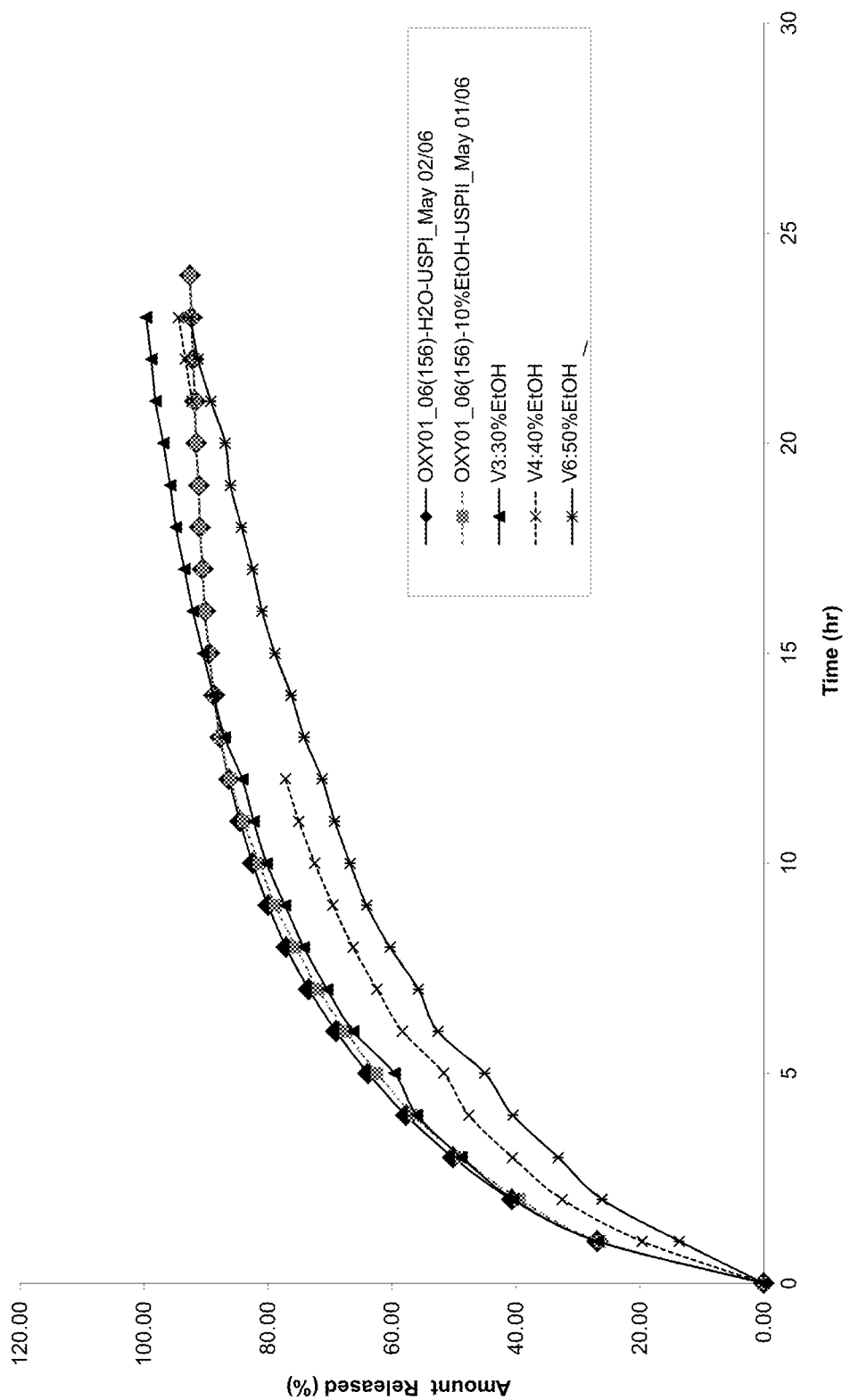

PHARMACEUTICAL COMPOSITION HAVING REDUCED ABUSE POTENTIAL

CROSS-REFERENCE TO RELATED APPLICATION

This application is a continuation of and claims priority to U.S. application entitled, "PHARMACEUTICAL COMPOSITION HAVING REDUCED ABUSE POTENTIAL," having Ser. No. 12/092,654, filed May 5, 2008, which claims priority to PCT patent application entitled, "PHARMACEUTICAL COMPOSITION HAVING REDUCED ABUSE POTENTIAL," having serial number PCT/CA2007/000862, filed May 14, 2007, which is a continuation-in-part of U.S. application entitled, "PHARMACEUTICAL COMPOSITION HAVING REDUCED ABUSE POTENTIAL", having Ser. No. 11/432,226, filed May 12, 2006, each of which is entirely incorporated herein by reference.

FIELD OF THE INVENTION

The present invention relates to a pharmaceutical composition comprising a controlled release agent. The present invention also relates to the use and method for making the same.

BACKGROUND OF THE INVENTION

Drug abuse has almost become a way of life to a rapidly growing segment of the world population, for example in the United States and Canada. It has become the vogue of many of the younger generation to experiment with any type of drug that will produce an emotional, psychological, euphoric, depressive or generally psychedelic experience.

A major problem is the abuse of medicinal opioid formulations by the parenteral route.

Another route of abuse which has become of serious concern is snorting of fine powder obtained from crushed opiod dosage form or the oral ingestion of finely crushed extended release oral dosage form in order to instantaneously obtain the benefit of the total opiod present in the slow release dosage form.

Another phenomenon that has become of concern regarding the use of extended release opiod analgesics is the discovery that they dose dump in the presence of alcohol and release all their content at once.

There has been a lot of concern with regards to the performance of extended release narcotics taught in prior art and currently commercialized. This is because the extended release or controlled release mechanism of current extended release opiod agonists using compositions and methods taught in the prior art is compromised and destroyed in the presence of alcohol leading to the loss of controlled release effects and complete release or dose dumping of its opiod content.

The danger and economic consequences of dose dumping in the presence of alcohol for current controlled release narcotic analgesics was highlighted when in Jul. 14, 2005 Purdue Pharma voluntarily took its pain-relieving narcotic analgesic Palladone (hydromorphone hydrochloride) capsules off the market. The company took the action on July 13 following an FDA request to withdraw Palladone because of safety concerns. The FDA approved Palladone in September 2004. The drug was launched by Purdue Pharma in February 2005. Palladone was approved for the management of persistent, moderate-to-severe pain in patients requiring continuous, around-the-clock pain relief with a high-potency opioid for an extended period of time. An FDA news release stated that serious and potentially fatal adverse reactions can occur when Palladone extended release capsules are taken together with alcohol.

According to an FDA news release, Palladone is a once-a-day pain management drug containing a very potent narcotic. New data gathered from a company-sponsored study testing the potential effects of alcohol use shows that when Palladone is taken with alcohol the extended release mechanism is harmed which can lead to dose-dumping. The FDA described dose-dumping, as the rapid release of the drug's active ingredient into the bloodstream. The agency's news release pointed out that dose-dumping, even with a low dose of Palladone (12 milligrams), could lead to "serious, or even fatal, adverse events in some patients". The FDA also warned that the risk increases for higher doses of Palladone.

Health Canada also issued an Advisory to warn of serious health risks associated with the consumption of alcohol while taking any slow-release opioid analgesics, following data from Purdue Pharma.

It can be argued that just like in the case of Palladone all powerful pain management drugs such as opiod agonists or narcotic analgesics have serious risks if used incorrectly, and this is particularly true for the current extended release formulations in the prior art or under commercialization. In fact Health Canada has advised patients receiving other slow-release opioids to be aware that these products may react in a similar way to hydromorphone slow release formulation when co-ingested with alcohol i.e., they may be released into the blood quickly (dose-dumping) instead of over extended release time periods, for example 24 hours.

This situation continues to present an unacceptably high level of patient risk. There is a great concern that as more patients take current compositions, safety problems will arise since even having one alcoholic drink could have fatal implications. The use of patient information vial label warnings regarding the dangers of using opioids and alcohol concomitantly is not expected to solve this problem. As a matter of fact the FDA has said that the agency doesn't believe that "potentially fatal, adverse events can be effectively managed by label warnings alone . . . "

Health authorities have turned up the heat and are demanding the pharmaceutical companies come clean and put interests of patients first. Accordingly, to investigate if the same effect occurs with other slow-release drugs, Health Canada requests that all manufacturers of these products provide information on the interaction between their drug and alcohol; if this is not possible, studies investigating product interactions with alcohol are to be conducted and completed within six months. Health Canada states that the data will be assessed within a three-month period and that further action will be taken if required.

From the foregoing there is therefore an urgent and great need for compositions of opiod agonist or narcotic analgesics or abuse-able substances which have a reduced potential for abuse or dose-dumping in the presence of alcohol.

Attempts have been made in the past to control the abuse potential associated with opioid analgesics. Parenteral dose of opioid analgesics are more potent as compared to the same dose administered orally. Therefore, drug abuse is often carried out by the extraction of the opioid from the dosage form, and the subsequent injection of the opioid (using any "suitable" vehicle for injection) in order to achieve a "high." Attempts to curtail abuse have therefore typically centered around the inclusion in the oral dosage form of an opioid antagonist which is not orally active but which will substantially block the analgesic effects of the opioid if one attempts to dissolve the opioid and administer it parenterally.

U.S. Pat. No. 3,254,088, describes the preparation of naloxone and its activity as a narcotic antagonist.

U.S. Pat. No. 3,493,657, describes the combination of morphine and naloxone as a composition for parenteral use "which has a strong analgesic, as well as antagonistic effect, without the occurrence of undesired or dangerous side effects."

A New York Times article appearing in a Jul. 14, 1970 issue described the oral administration of naloxone to narcotic addicts as a method of treatment. The oral administration of naloxone (in high doses) "makes it impossible for the addict to experience a high no matter how much heroin he uses."

The combination of pentazocine and naloxone has been utilized in tablets available in the United States, commercially available as Talwin™ from Sanofi-Winthrop. Talwin™ contains pentazocine hydrochloride equivalent to 50 mg base and naloxone hydrochloride equivalent to 0.5 mg base. Talwin™ is indicated for the relief of moderate to severe pain. The amount of naloxone present in this combination has no action when taken orally, and will not interfere with the pharmacologic action of pentazocine. However, this amount of naloxone given by injection has profound antagonistic action to narcotic analgesics. Thus, the inclusion of naloxone is intended to curb a form of abuse of oral pentazocine which occurs when the dosage form is solubilized and injected. Therefore, this dosage has lower potential for parenteral abuse than previous oral pentazocine formulations. However, it is still subject to patient misuse and abuse by the oral route, for example, by the patient taking multiple doses at once.

Sunshine, et al. "Analgesic Efficacy of Pentazocine Versus a Pentazocine-Naloxone Combination Following Oral Administration", Clin. J. Pain, 1988:4:35-40, reported on the effect of the addition of 0.5 mg naloxone on the analgesic efficacy of pentazocine 50 mg. The combination was found to be significantly less efficacious than pentazocine for the sum of the pain intensity difference (SPID), and for relief and pain intensity difference (PID) at the fourth hour. For patients with moderate baseline pain, the combination produced significantly less pain relief than pentazocine for SPID and for relief and PID at hours 3 and 4. In patients with severe baseline pain, there was no significant difference found between pentazocine and the combination of pentazocine plus naloxone.

Wang, et al. "Crossover and Parallel Study of Oral Analgesics", J. Clin Pharmacol 1981; 21:162-8, studied the combination of naloxone 0.25 mg and Percodan™ (composed of 4.5 mg oxycodone HC1, oxycodone terephthalate 0.28 mg, aspirin 224 mg, phenacetin 160 mg, and caffeine 32 mg) compared to Percodan™ alone, and placebo in a crossover study of patients with chronic pain. The combination had lower mean scores than Percodan™ alone for most of the analgesic hourly parameters in the later hours of the trial. However, for the summary variables, the combination showed no significant difference from either placebo or Percodan™.

A fixed combination of buprenorphine and naloxone was introduced in 1991 in New Zealand (Temgesic™, Reckitt & Colman) for the treatment of pain.

A fixed combination therapy comprising tilidine (50 mg) and naloxone (4 mg) has been available in Germany for the management of severe pain since 1978 (Valoron™, Goedecke). The rationale for the combination of these drugs is effective pain relief and the prevention of tilidine addiction through naloxone-induced antagonisms at the morphine receptor.

U.S. Pat. No. 3,773,955 (Pachter, et al.) described orally effective analgesic compositions which upon parenteral administration do not produce analgesia, euphoria, or physical dependence, and thereby prevent parenteral abuse of the analgetic agents. Such compositions contained from about 0.1 mg to about 10 mg naloxone per analgetic oral dose. This reference was not concerned with oral abuse of opioids.

U.S. Pat. No. 3,493,657 (Lewenstein, et al.) described compositions comprising naloxone and morphine or oxymorphone, which compositions were said to provide a strong analgesic effect without the occurrence of undesired side effects such as hallucinations.

U.S. Pat. No. 4,457,933 (Gordon, et al.) described a method for decreasing both the oral and parenteral abuse potential of strong analgesic agents such as oxycodone, propoxyphene and pentazocine, by combining an analgesic dose of the opioid with naloxone in a specific, relatively narrow range. Oxycodone-naloxone compositions having a ratio of 2.5-5:1 parts by weight and pentazocine-naloxone compositions having a ratio of 16-50:1 parts by weight were preferred. The dose of naloxone which was to be combined with the opioid is stated to substantially eliminate the possibility of either oral or parenteral abuse of the opioid without substantially affecting the oral analgesic activity thereof.

U.S. Pat. No. 4,582,835 (Lewis) describes a method of treating pain by administering a sublingually effective dose of buprenorphine with naloxone. Lewis describes dosage ratios of naloxone to buprenorphine from 1:3 to 1:1 for parenteral administration, and from 1:2 to 2:1 for sublingual administration.

U.S. Pat. No. 6,627,635 teaches a method of preventing abuse of opioid dosage forms wherein an analgesically effective amount of an orally active opioid agonist is combined with an opioid antagonist into an oral dosage form which would require at least a two-step extraction process to be separated from the opioid agonist, the amount of opioid antagonist including being sufficient to counteract opioid effects if extracted together with the opioid agonist and administered parenterally.

U.S. Pat. No. 6,696,088 discloses tamper-resistant oral opioid agonist formulations comprising (i) an opioid agonist in releasable form and (ii) a sequestered opioid antagonist which is substantially not released when the dosage form is administered intact, such that the ratio of the amount of antagonist released from said dosage form after tampering to the amount of said antagonist released from said intact dosage form is about 4:1 or greater, wherein said agonist and antagonist are interdispersed and are not isolated from each other in two distinct layers.

Despite all the above attempts in the prior art to address the problem of drug abuse, the problem persists partly because of design faults in the compositions and the addicts coming up with creative ways to beat the anti drug abuse mechanism. At present the problem is escalating at an alarming rate with devastating financial and social consequences.

Therefore, there is still a need to develop a stable drug delivery device that can be reproducibly manufactured and have a desired effect of reducing potential for abuse.

SUMMARY OF THE INVENTION

An object of one aspect of the present invention is to provide a composition that can be effectively employed to control the release of an active substance.

An object of a second aspect of the present invention is to provide a composition that can be effectively employed to reduce the problem of dose dumping of an active substance.

An object of a third aspect of the present invention is to provide a composition that can be effectively employed to reduce the potential for abuse of an active substance.

In accordance with an aspect of the present invention, there is provided a pharmaceutical paste composition comprising an active substance and materials selected from clays, controlled release agents or oily, waxy or fatty substances in an amount and ratio which is sufficient to prevent the compromising or loss of integrity of the controlled release mechanism of the composition upon oral administration or co-ingestion with alcohol.

In accordance with another aspect of the present invention, there is provided a means for preventing dose dumping in the presence of alcohol and the prevention of the abuse of oral formulations of therapeutically valuable active substances by admixing such substances with materials selected from clays, oily, waxy or fatty substances or controlled release agents.

In accordance with yet another aspect of the present invention, there is provided a controlled release composition and method in which the physicochemical nature of the composition helps to prevent dose dumping in the presence of alcohol and also discourage abuse and make it harder to abuse by mode of crushing, milling or grinding and dissolving, heating to cause evaporation and snorting, "shooting" or inhalation.

In accordance with still another aspect of the present invention, there is provided a pharmaceutical paste composition comprising: i) an active substance; ii) an oily, waxy, or fatty substance, or a combination thereof; and iii) a controlled release agent; wherein the paste composition is non-newtonian, thixotropic and/or pseudoplastic.

In accordance with still another aspect of the present invention, there is provided a pharmaceutical paste composition comprising: i) an active substance; ii) a controlled release agent; and iii) a non-aqueous vehicle; wherein the paste composition is non-newtonian, thixotropic and/or pseudoplastic.

In accordance with still another aspect of the present invention, there is provided a pharmaceutical paste composition comprising: i) an active substance; ii) a clay; and iii) a controlled release agent; and iv) a non-aqueous vehicle; wherein the paste composition is non-newtonian, thixotropic and/or pseudoplastic.

In accordance with still another aspect of the present invention, there is provided a pharmaceutical paste composition comprising: i) an addictive substance; ii) an oily, waxy, or fatty substance, or a combination thereof; and iii) a controlled release agent; wherein the paste composition is for use in a dosage form dispensing device.

In accordance with still another aspect of the present invention, there is provided a pharmaceutical paste composition comprising: i) an addictive substance; ii) a controlled release agent; and iii) a non-aqueous vehicle; wherein the paste composition is for use in a dosage form dispensing device.

In accordance with still another aspect of the present invention, there is provided a pharmaceutical paste composition comprising: i) an addictive substance; ii) a clay; and iii) a controlled release agent; and iv) a non-aqueous vehicle; wherein the paste composition is for use in a dosage form dispensing device.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

BRIEF DESCRIPTION OF THE DRAWINGS

The following drawings are illustrative of embodiments of the invention and are not meant to limit the scope of the invention as encompassed by the claims:

FIG. 1 shows, in accordance with an embodiment of the invention, data regarding the release of an active pharmaceutical ingredient over a sustained-release period in varying concentrations of alcohol.

DETAILED DESCRIPTION OF THE INVENTION

Certain embodiments of the present invention relate to a novel composition and to a method of using and preparing same in order to reduce the potential for abuse of an addictive substance. This is accomplished by the use of a paste composition. The addictive substance may be, without limitation, an opiod agonist, a narcotic analgesic, barbiturates, central nervous system stimulants, and/or tranquilizers. Prior to incorporation within a paste, an addictive substance may be in any suitable form known in the art, liquid, semi-solid or solid, for example, without limitation, powder, granules, spheroids, pellets, microspheres, nanospheres, microcapsules, or crystals, and may be homogenously or non-homogenously dispersed in the paste.

The novel composition of the present invention can be used in any delivery device such as, and without being limited thereto, a sustained release, pulsed release, delayed release and/or controlled release device that controls the release of one or more active pharmaceutical ingredients. The device can be a solid unit dosage form. The device can comprise a paste that comprises, for example, one or more granules, one or more crystals, one or more pellets and/or one or more spheroids. In a specific embodiment, the device is a stable single homogeneous unit controlled release device which controls the release rate, without significant variability, and with a reproducible controlled release rate.

The composition may be administered in any suitable manner using any suitable formulation and/or dispensing device. For example and without being limited thereto, the composition can be in the form of a suitable device for in vivo oral, vaginal, anal, ocular, subcutaneous, intramuscular administration or for implantation. The composition may also be used for in vitro or ex vivo delivery of an addictive substance. It may be targeted at specific sites in the gastrointestinal tract or to specific organs. It may be applied buccally and transdermally in a pouch or patch. It is evident that the physical state of the formulation and the particular method of application may vary accordingly.

Paste compositions may be useful in formulation of addictive substances to reduce the abuse potential of the addictive substance, for example via alcohol extraction. However, it will be understood that the utility of paste compositions may not be limited to addictive substances, and may also be useful in formulation of any active ingredient or substance.

The term "active ingredient" or "active substance" means any compound which has biological, chemical, or physiological utility including, without limitation, active pharmaceutical ingredient, drug, naturally occurring compound, nucleic acid compound, peptide compound, nutraceutical, agricultural or nutritional ingredient or synthetic drug.

The term "addictive substance" means any compound upon which a user may develop a psychic or physical dependence, including, without limitation, active pharmaceutical ingredient, drug, naturally occurring compound, or synthetic drug.

Many interchangeable terms are commonly used to describe the psychic or physical dependence of people upon compounds. The term addiction is most commonly used when talking about the strong analgesics or opiod agonist or abuse-able substances. The strong analgesics or opiod agonist or abuse-able substances, in contrast to the weaker agents such as aspirin, acetaminophen, and the like, are employed in the relief of more severe pain. They usually produce a euphoric effect when crushed and swallowed, snorted and "shoot" parenterally. When taken as oral controlled release composition there is usually no significant euphoria.

Addiction can develop to the barbiturates and strong analgesic agents or opiod agonist or abuse-able substances, in the sense of the term "addiction" as defined by the Committee on Problems of Drug Dependence of The National Research Council, namely, a compulsion to take the drug and to increase the dose, with the development of psychic and sometimes physical dependence on the effects of the drug, so that the development of means to continue the administration of the drug becomes an important motive in the addict's existence.

Addiction to narcotics or narcotic-like strong analgesics often occurs by the legitimate chronic oral or parenteral administration of these agents in the alleviation of deep pain. More commonly, however, addiction to these agents occurs when the psychologically unbalanced or thrill-seeking individual looking for an escape from the realities of life finds his escape in the euphoria produced by the oral or parenteral administration of strong analgesics or opiod agonist or abuse-able substances. Euphoria is generally defined as a feeling of well-being. Euphoria can be produced in many ways, e.g., an exhilarating experience, alcohol, stimulants, depressants, narcotics, etc. For the purpose of this disclosure, "euphoria" is defined as an abnormal state of well-being produced by the parenteral administration of strong analgesics.

Addictive substance encompasses the terms "abuse-able substances", "euphoric analgesics" and "strong analgesics," often called narcotic or narcotic-like analgesics or opiod agonist, including, for example, those chemical agents which upon oral or parenteral administration are capable of maintaining or partially maintaining a known addict addicted to heroin or the like without substantial withdrawal symptoms. For the purpose of this disclosure, a "strong analgesic" can also be described as any analgesic agent whose analgesic, euphoric or dependence producing actions are negated by the parenteral administration of an opiod antagonist.

Examples of some of the opiod agonists or narcotic analgesics contemplated for use in this invention include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tramadol, tilidine, alphaprodine, dextroporpoxyphene, propiram, profadol, phenampromide, thiambutene, pholcodeine, 3-trans-dimethylamino-4-phenyl-4-trans-carbethoxy-delta-cyclohexene, 3-di methylamino-O-(4-methoxyphenylcarbamoyl)-propiophenone oxime, (−)beta-2'-hydroxy-2,9-dimethyl-5-phenyl-6,7-benzomorphan, (−)2'-hydroxy-2-(3-methyl-2-butenyl)-9-methyl-5-phenyl-6,7-benzomorphan, pinnitramide, (−)alpha-5,9-diethyl-2'-hydroxy-2-methyl-6,7-benzomorphan, ethyl-1-(2-dimethylaminoethyl)-4,5,6,7-tetrahydro-3-methyl-4-oxo-6-phenyl-indole-2-carboxylate, 1-Benzoylmethyl-2,3-dimethyl-3-(m-hydroxyphenyl)-piperidine, N-allyl-7alpha-(1-(R)-hydroxy-1-methylbutyl)-6,14-endo-ethanotetrahydron ororipavine, (−)2'-hydroxy-2-methyl-6,7-benzomorphan, noracylmethadol, phenoperidine, alpha-dl-methadol, beta-dl-methadol, alpha-1-methadol, beta-dl-acetylmethadol, alpha-1-acetylmethadol and beta-1-acetylmethadol and pharmaceutically acceptable salts thereof, stereoisomers thereof, ethers thereof, esters thereof, and mixtures thereof.

Addictive substances also include drugs most commonly employed for illicit purposes (to bring about a "high", euphoria, excitement, stupor, sleep deprivation etc.) such as the barbiturates, lysergic acid diethylamide (LSD), mescaline, marijuana (tetrahydrocannabinol), heroin, and the like, the central nervous system stimulants (the amphetamines and the like) sedative, hypnotics and some of the major and minor tranquilizers (the promazines, meprobamate, the diazepines, and the like).

Many addictive substances are commonly used in medicine for the legitimate treatment of various conditions and therefore have a limited availability in our society. While these agents are a necessary part of modern medicine, it would be highly desirable (1) to produce new drugs that have reduced drug abuse potential or (2) to "denature" the old agents to prevent their illicit use. The pharmaceutical industry has been striving to achieve the first goal for many years but most regrettably has only achieved very moderate success. If one focuses on the strong analgesics, it becomes apparent that much effort and money has been expended to produce chemicals possessing good analgesic activity but little or no addictive liability. While good progress has been made as evidenced, for example, by the development of propoxyphene as a replacement for codeine and pentazocine as a replacement for morphine or meperidine, these compounds are still reported in the medical literature to be addictive and/or euphoric and subjected to abuse by crushing and dissolving and heating/evaporation of the drug composition to enable immediate access to the drug by swallowing, inhalation, snorting, "shooting" or parenteral administration. Furthermore, some of these agents have undesirable side effects, i.e., bad hallucinations, etc.

The compositions or devices of the present invention can also contain other active ingredients. These include, amongst others and for example, opiod antagonists (such as naloxone), aspirin, phenacetin, caffeine, acetaminophen, antihistamines, homatropine methylbromide, phenyltoloxamine citrate, barbiturates, or the like, or multiple combinations thereof. Also included within the scope of the present invention are those compositions comprising narcotic analgesics in combination with non narcotic analgesics, antitussive preparations which contain narcotic or narcotic-like cough suppressants such as codeine, dihyrocodeinone, pholcodeine, and the like. Other products comprising a narcotic or narcotic-like composition for use as an antispasmotic in the gastrointestinal tract, such as Camphorated Opium Tincture, U.S.P., Opium Tincture, U.S.P., Opium extract, N.F., and the like can be an integral part of certain examples of the present invention.

The term "paste" means a pharmaceutical form of thick or stiff consistency. A paste may also comprise solids of less than 1000 microns dispersed therein. A paste can also be described as a liquid or semi-solid matrix or magma or paste which is non-newtonian, thixotropic or pseudoplastic. A paste typically comprises an addictive substance. However, a paste may comprise other active ingredients with or without the presence of an addictive substance. Furthermore, a singular paste composition may be used or combinations of two or more paste compositions having different release profiles and/or comprising different active substances may be used. The release profiles provided by the paste compositions of the present invention may be advantageously used in the formulation of any active ingredient.

Two or more populations of pastes with different release properties in a singular or multiple dosage unit(s) may be used for delivery of the active substances. One or more active substances can be delivered similarly, by use of multiple paste populations. For example, formulating two active substances in two paste compositions, respectively may be particularly useful if the substances are incompatible or are to act separately or at different onset of action. The different population of paste can be encapsulated or delivered in any other suitable holding or dispensing device.

A paste may comprise one or more controlled release agent, and/or one or more clays such as bentonite and/or one or more fillers in a pharmaceutically suitable vehicle, and optionally materials selected from disintegrants, humectants, surfactants and stabilizers. In certain examples, a paste may comprise one or more controlled release agent, and/or one or more clays such as bentonite and/or one or more fillers in a non-aqueous vehicle, and optionally materials selected from disintegrants, humectants, surfactants and stabilizers. In certain examples, a paste may comprise one or more controlled release agent, and/or one or more clays such as bentonite and/or one or more fillers in an aqueous vehicle, optionally comprising an emulsifier for mixing with oily, fatty or waxy substances, and optionally materials selected from disintegrants, humectants, surfactants and stabilizers.

A paste composition may be formulated such that physicochemical properties of the paste reduces or prevents dose dumping of active substances. For example, a paste composition may be formulated such that physicochemical properties of the paste reduces or prevents dose dumping of addictive substances in the presence of alcohol, and discourages drug abuse by mode of crushing, milling or grinding the dosage form to powder or heating the dosage form to vapour and snorting or inhalation by the nasal route or dissolving to abuse via the parenteral route.

The term "polymeric coating" or "polymeric coat" means any coating which is formed by polymerization of one or more monomers to form linear or branched or cross-linked macromolecules. The coating may be variously characterized as a coating, layer, membrane, shell, capsule, or the like, and substantially surrounds or envelope a core particle. Where a device of the present invention comprises more than one polymeric coat, a first polymeric coat substantially surrounds or envelopes a core particle, a second polymeric coat substantially surrounds or envelopes the first polymeric coat, and so forth. Polymeric coats may take the form and composition of any known compatible controlled-release coat, for example a pH sensitive coat, a water repellant coat, or an aqueous solvent based coat, or a water soluble coat.

In certain examples, a polymeric coat may be prepared from a homogenous mixture comprising a water soluble gel forming polymer and a water insoluble organosoluble polymer in an organosolvent. While such a preparation may be substantially non-aqueous, small amounts of water may be used or tolerated, for example, less than about 20% (v/v), less than about 10% (v/v), less than about 5% (v/v) or less than about 2% (v/v) of the polymeric coating composition before application to or incorporation into the controlled-release delivery device.

The terms "sustained release", "pulsed release", "delayed release" and "controlled release" are used interchangeably in this application and are defined for purposes of the present invention as the release of an active ingredient from a delivery device at such a rate that when a dose of the active ingredient is administered in the sustained release, pulsed release, delayed release or controlled-release device, concentrations (levels) of the active ingredient are maintained within a desired range but below toxic levels over a selected period of time. In the case of in vivo administration, concentrations (levels) of the active ingredient could be measured in blood or plasma, for example. When administered in vivo the sustained release, pulsed release, delayed release or controlled-release device of the present invention allows for useful plasma concentration of an active ingredient to be maintained for longer than in the case of immediate-release forms.

The controlled release profile may be modified on the basis of many factors pertaining to the polymeric coats, for example, without limitation, through the types of polymers used, the order in which they are deposited, the ratios of the polymers in the mix and the nature of their interaction. The controlled-release profile can also be modified by a variety of factors relating to the delivery device and the route of administration as outlined for example, in US Application No. 20070003619, published Jan. 4, 2007. For example, the sustained-release period will vary depending upon the solubility of the active ingredient, the rate of clearance of the active ingredient from the intended site of administration, the size of the core particle, the amount of the active ingredient initially present in the core particle, the presence of other compounds within the core particle that affect the rate of release of the active ingredient, the permeability of the polymeric coating(s) to the active pharmaceutical ingredient, and the rate of degradation of the polymeric coating(s), as well as other factors.

Release control may be effected or optimized through the types of polymers used, the order in which they are deposited, the number of polymeric coats, the width of polymeric coats, the ratios of the polymers in the mix and the nature of their interaction.

It is commonly known to the narcotic enforcement agencies and others in the medical trades that a substantial amount of the strong analgesics destined for legitimate medicinal use are diverted to illicit use through dishonest or careless handling. In many instances, these drugs are obtained by the addict or potential addict by theft or casual prescribing practice by the physician.

It is known from experience that the true narcotic addict must feed his habit by the crushing and/or dissolving and heating and/or evaporation of the drug composition to enable immediate access to the drug by swallowing, inhalation, snorting, "shooting" or parenteral route (mainlining) to obtain the maximum euphoric effect. The potential addict or thrill-seeker will also experiment in the same manner. Unfortunately, a substantial amount of the legitimate strong analgesics formulated in oral dosage form are diverted to illicit parenteral use. Since the oral dosage forms of these drugs diverted from legitimate channels must be easily crushed, dissolved and heated/evaporated in order to get a form in which it can be administered to produce the desired euphoria, it follows that if these oral dosage forms are in some way rendered difficult or impossible to crush, dissolve, heat/evaporate or extract and made unpleasant for abuse via swallowing, snorting, inhalation and "shooting" or parenteral use the addict or potential addict will be cut off from this particular supply of euphoric drugs. Obviously, oral activity must be retained if a useful medicament is to be provided.

Incorporating a pharmaceutical drug, that is an addictive substance, in a paste composition may be useful for (1) reducing at least one mode of abuse, for example, the illicit use by snorting/inhalation, parenteral administration, or crushing and oral ingestion of dosage forms intended for oral administration; (2) reducing dose dumping, for example in the presence of alcohol; or (3) timed or extended release compositions and/or devices which despite its pseudoplastic or thixotropic nature maintains its integrity sufficiently to perform its controlled release functions during transit in the GIT.

Paste compositions and comprise an addictive substance materials selected from oily, waxy or fatty substances, clays or controlled release agents can discourage abuse and make it harder to abuse by mode of crushing, dissolving, heating to cause evaporation and snorting, "shooting" or inhalation.

Paste compositions may optionally comprise a pharmaceutically acceptable nasal irritant. A nasal irritant can produce nasal irritation and annoyance feeling when the composition is brought in contact with the nasal membrane. The irritant agent is not in amounts sufficient to precipitate allergic type reactions or immune response upon snorting. U.S. Pat. No. 7,157,103 (Sackler) issued Jan. 2, 2007, suggests the use of various irritants in preparing pharmaceutical formulations including, for example, capsaicin, a capsaicin analog with similar type properties as capsaicin, and the like. Some capsaicin analogues or derivatives include for example, resiniferatoxin, tinyatoxin, heptanoylisobutylamide, heptanoyl guaiacylamide, other isobutylamides or guaiacylamides, dihydrocapsaicin, homovanillyl octylester, nonanoyl vanillylamide, or other compounds of the class known as vanilloids. Resiniferatoxin is described, for example, in U.S. Pat. No. 5,290,816 (Blumberg), issued Mar. 1, 1994. U.S. Pat. No. 4,812,446 (Brand), issued Mar. 14, 1989, describes capsaicin analogs and methods for their preparation.

With the inclusion of an irritant (e.g., capsaicin) in a dosage form, when the dosage form is tampered with, the capsaicin imparts a burning or discomforting quality to the abuser to preferably discourage the inhalation, injection, or oral administration of the tampered dosage form, and preferably to prevent the abuse of the dosage form. Suitable capsaicin compositions include capsaicin (trans 8-methyl-N-vanillyl-6-noneamide) or analogues thereof in a concentration between about 0.00125% and 50% by weight, preferably between about 1 and about 7.5% by weight, and most preferably, between about 1 and about 5% by weight of the dosage form.

Paste compositions are formulated such that an addictive substance comprised therein is not easily soluble and immediately available upon crushing and attempt at dissolving it for intravenous injection or to get access to the total drug immediately upon oral ingestion of the crushed dosage form is not met with easy success.

A paste composition makes it harder for dose dumping of an addictive substance in the presence of alcohol or during co-ingestion of alcohol. For example, FIG. 1 shows that a controlled release profile a paste composition comprising oxycodone is maintained in varying concentrations of ethanol.

A paste composition will typically comprise a controlled release agent or an oily, fatty or waxy substance, or a clay. When present in a paste composition the concentration of a controlled release agent may be from about 2% to about 90%. When present in a paste composition the concentration of an oily substance may be from about 3% to about 99%. When present in a paste composition the concentration of a fatty substance may be from about 0.5% to about 70%. When present in a paste composition the concentration of a waxy substance may be from about 0.5% to about 70%. When present in a paste composition the concentration of a clay may be from about 0.1% to about 95%.

Examples of clays suitable for use in a paste composition are bentonite, veegum and other clay minerals such as phyllosilicates (Smectite, illite, sepiolite, palygorskite, muscovite, allevardite, amesite, hectorite, fluorohectorite, saponite, beidellite, talc, nontronite, stevensite, mica, vermiculite, fluorovermiculite, halloysite and fluorine-containing synthetic types of mica, phyllosilicates, beidellite; volkonskoite; hectorite; sauconite; sobockite; svinfordite; and the like. Other useful materials include micaceous minerals, such as mixed illite/smectite minerals, such as rectorite, tarosovite, ledikite and admixtures of illites with the clay minerals named above. A swelling bentonite is preferred.

U.S. Pat. No. 4,517,112 teaches Modified organophilic clay complexes, their preparation and non-aqueous systems containing them and more especially, organophilic organic-clay complexes which are dispersible in organic liquids to form a gel therein, which comprises the reaction product of (a) a smectite-type clay having a cation exchange capacity of at least 75 milliequivalents per 100 grams of said clay; (b) a primary anion selected from the group consisting of anions derived from organic sulfonic acids, alkylsulfates and mixtures thereof containing at least one lineal or branched alkyl group having greater than 9 carbon atoms, aromatic sulfonic acids and mixtures thereof; (c) a secondary anion different from said primary anion and selected from the group consisting of anions derived from organic acids having a pKa of less than about 11.0 and mixtures thereof; and (d) an organic cation is an amount sufficient to satisfy the cation in exchange capacity of said clay and the cationic activity of the primary and secondary anions wherein the resulting organic cation-organic anion complexes are intercalated with the smectite-type clay and wherein the combination of said primary and secondary anion synergistically increases the ease of dispersion of said organophilic clay gellant in an organic liquid. This invention relates to compositions gels which may be useful as lubricating greases, oil base muds, oil base packer fluids, paint-varnish-lacquer removers, paints, foundry molding sand binders, adhesives and sealants, inks, polyester laminating resins, polyester gel coats, and the like.

U.S. Pat. No. 4,676,929 describes useful gels generated from expandable, hydrated sheet silicates, also known as lattice layered silicates, or phyllosilicates. It is also concerned with articles of manufacture produced by further treatment of such gels, and with methods of generating and treating the gels. The silicate minerals of interest include vermiculite, beidellite, nontronite, volchonskoite, saponite, stevensite, sauconite, pimelite, bentonite, montmorillonite, hectorite, the smectites, attapulgite, sepiolite, phlogopite and biopyrobole; i.e., in essence the entire genus of hydrated or hydratable phyllosilicates whether of natural or synthetic origin.

When present in a paste composition the concentration of a clay may be from about 0.1% to about 95%. In certain examples, the amount of clay may be from about 0.5% to about 20% (w/w) based on the total weight of the paste composition. In other examples, the amount of clay may be from about 0.8% to about 20% (w/w) based on the total weight of the paste composition. In still other examples, the amount of clay may be from about 1% to about 20% (w/w) based on the total weight of the paste composition.

Oily, fatty or waxy components may also be used in a paste composition and include any pharmaceutically acceptable oily, fatty or waxy substance that is insoluble or substantially insoluble in ethanol or water. These include oils and fats, waxes, hydrocarbons, higher fatty acids, higher alcohols, esters, metal salts of higher fatty acids, and the like. Specific examples of oils and fats include plant oils, e.g. cacao buffer, palm oil, Japan wax (wood wax), coconut oil, corn oil, etc.; animal oils, e.g. beef tallow, lard, horse fat, mutton tallow, etc.; hydrogenated oils of animal origin, e.g. hydrogenated fish oil, hydrogenated whale oil, hydrogenated beef tallow, etc.; hydrogenated oils of plant origin, e.g. hydrogenated corn oil, hydrogenated rape seed oil, hydrogenated castor oil, hydrogenated coconut oil, hydrogenated soybean oil, etc.; and the like. Of these hydrogenated oils are preferred as an oil component of the present invention. Specific examples of waxes include plant waxes, e.g. carnauba wax, candelilla wax, bayberry wax, auricurry wax, espalt wax, etc.; animal waxes, e.g. bees wax, breached bees wax, insect wax, spermaceti, shellac, lanolin, etc.; and the like. Of these preferred are carnauba wax, white beeswax and yellow beeswax. Paraffin, petrolatum, microcrystalline wax, and the like, are given as specific examples of hydrocarbons, with preferable hydrocarbons being paraffin and microcrystalline wax. Given as examples of higher fatty acids are caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, and the like. Of these, preferable are myristic acid, palmitic acid, stearic acid, and behenic acid. Specific examples of higher alcohols are lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, corianyl alcohol, ceryl alcohol, and myricyl alcohol. Particularly preferable alcohols are cetyl alcohol, stearyl alcohol, and the like. Specific examples of esters are fatty acid esters, e.g. myristyl palmitate, stearyl stearate, myristyl myristate, behenyl behenate, ceryl lignocerate, lacceryl cerotate, lacceryl laccerate, etc.; glycerine fatty acid esters, e.g. lauric monoglyceride, myristic monoglyceride, stearic monoglyceride, behenic monoglyceride, oleic monoglyceride, oleic stearic diglyceride, lauric diglyceride, myristic diglyceride, stearic diglyceride, lauric triglyceride, myristic triglyceride, stearic triglyceride, acetylstearic glyceride, hydroxystearic triglyceride, etc.; and the like. Specific examples of metal salts of higher fatty acid are calcium stearate, magnesium stearate, aluminum stearate, zinc stearate, zinc palmitate, zinc myristate, magnesium myristate, and the like.

In certain examples, the oils used in the invention may be one or more selected from Almond Oil, Apricot Kernel Oil, Avocado Oil, Black Currant Oil, 14% GLA, Borage Oil, 20% GLA, Canola Oil, Carrot Oil, Castor Oil, Clove Leaf Oil, Coconut Oil, Corn Oil, Cottonseed Oil, Evening Primrose Oil, 9% GLA, Flaxseed Oil, 55% ALA, Grapeseed Oil, Hazelnut Oil, Hemp Oil, ALA/GLA, Hydrogenated Oils, Jojoba Oil, Golden Jojoba Oil, Water-white Kukui Nut Oil, Macadamia Nut Oil, Oat Oil, Olive Oil, Extra Virgin Olive Oil Pomace/"B" grade, Olive Oil, Pure/NF, Palm Oil, Parsley Seed Oil, Peach Kernel Oil, Peanut Oil, Pecan Oil, Pistachio Oil, Pumpkinseed Oil, Rice Bran Oil, Rose Hip Seed Oil, Rosemary Oil, Safflower Oil, Linoleic' Safflower Oil, High-Oleic, Sesame Oil NF, Sesame Oil Toasted, Soybean Oil, Sunflower Oil, Salad Sunflower Oil High-Oleic, Tea Tree Oil, Vegetable, Glycerine, USP, Walnut Oil, Wheat Germ Oil, Cold-pressed and mineral oil or other similar oils.

Controlled release agents that may be used in the composition of this invention include naturally occurring or synthetic, anionic or nonionic, hydrophobic, hydrophilic rubbers, polymers, starch derivatives, cellulose derivatives, polysaccharides, carbomer, resins, acrylics, proteins, vinylpyrrolidone-vinyl-acetate-copolymers, galactomannan and galactomannan derivatives, carrageenans and the like. Specific examples are acacia, tragacanth, Xanthan gum, locust bean gum, guar-gum, karaya gum, pectin, arginic acid, polyethylene oxide, polyethylene glycol, propylene glycol arginate, hydroxypropyl methylcellulose, methylcellulose, hydroxypropyl cellulose, hydroxyethyl cellulose, carboxymethylcellulose sodium, polyvinylpyrrolidone, carboxyvinyl polymer, sodium polyacrylate, alpha starch, sodium carboxymethyl starch, albumin, dextrin, dextran sulfate, agar, gelatin, casein, sodium casein, pullulan, polyvinyl alcohol, deacetylated chitosan, polyethyoxazoline, poloxamers, ethylcellulose, chitin, chitosan, cellulose esters, aminoalkyl methacrylate polymer, anionic polymers of methacrylic acid and methacrylates, copolymers of acrylate and methacrylates with quaternary ammonium groups, ethylacrylate methylmethacrylate copolymers with a neutral ester group, polymethacrylates, surfactants, aliphatic polyesters, zein, polyvinyl acetate, polyvinyl chloride, and the like.

A pharmaceutically acceptable acrylic polymer may also be used in certain examples. Specific examples include, but are not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly(methyl methacrylate), poly(methyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH independent or pH dependent.

When present in a paste composition the concentration of a controlled release agent may be from about 2% to about 90%. In certain examples, in order to achieve the desired controlled release effect, the lower limit of the controlled release agent may be greater than 2%, for example, at least about 5%, 10%, 15%, or 20% (w/w) based on the total weight of the paste composition with the upper limit typically being less than 60% (w/w).

The controlled release profile of a paste composition may be modified on the basis of many factors pertaining to the controlled release agent, for example, without limitation, through the types of agents used, the order in which they are deposited, the ratios of the agents in the mix and the nature of their interaction.

Further examples of additives that may be used in the composition of the invention include, but are not limited to, ethyl lactate, phthalates such as dimethyl phthalate (DMP), diethyl phthalate (DEP), dibutyl phthalate (DBP), dioctyl phthalate, glycol ethers such as ethylene glycol diethyl ether, propylene glycol monomethyl ether, PPG-2 myristyl ether propionate, ethylene glycol monoethyl ether, diethylene glycol monoethyl ether, propylene glycol monotertiary butyl ether, dipropylene glycol monomethyl ether, N-methyl-2-pyrrolidone, 2 pyrrolidone, isopropyl myristate, isopropyl palmitate, octyl palmitate, di methylacetamide, propylene glycol, propylene glycol monocaprylate, propylene glycol caprylate/caprate, propylene glycol monolaurate, glycofurol, linoleic acid, linoeoyl macrogol-6 glycerides, oleic acid, oleic acid esters such as glyceryl dioleate, ethyl oleate, benzoic acid, oleoyl macrogol-6 glycerides, esters such as ethylbenzoate, benzylbenzoate, sucrose esters, sucrose acetate isobutyrate, esters of lactic acid, esters of oleic acid, sebacates such as dimethyl sebacate, diethyl sebacate, dibutyl sebacate, dipropylene glycol methyl ether acetate (DPM acetate), propylene carbonate, propylene glycol laurate, propylene glycol caprylate/caprate, gamma butyrolactone, medium chain fatty acid triglycerides, glycerol and PEG esters of acids and fatty acids, PEG-6 glycerol mono oleate, PEG-6 glycerol linoleate, PEG-8 glycerol linoleate, caprylic acid esters such as caprylocapryl macrogol-8 glycerides, PEG-4 glyceryl caprylate/caprate, PEG-8 glyceryl caprylate/caprate, polyglyceryl-3-oleate, polyglyceryl-6-dioleate, polyglyceryl-3-isostearate, polyglyceryl polyoleate, decaglyceryl tetraoleate and glyceryl triacetate, glyceryl monooleate, glyceryl monolinoleate, dimethylformamide, dimethylsulfoxide, tetrahydrofuran, caprolactam, decylmethylsulfoxide, and, 1-dodecylazacycloheptan-2-one. The invention may contain surface active agents with varying hydrophilic lipophilic balance (HLB) values such as polyoxyethylene castor oil, polyoxyethylene hydrogenated castor oil, polyoxyethylene sorbitan fatty acid esters, polyoxyethylene alkyl esters, polyoxyethylene alkyl ethers, polyoxyethylene glycerol esters, sorbitan fatty acid esters, and sodium lauryl sulphate.

Examples of antioxidants that may be used in this invention is selected from ascorbic acid, fumaric acid, malic acid, alpha tocopherol, ascorbic acid palmitate, butylated hydroxyanisole, propyl gallate, sodium ascobate, and sodium metabisulfite or other suitable antioxidants and stabilizers.

Examples of plasticizers that may be used in this invention include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%, and preferably about 0.1% to about 20% of the plasticizer can be used. The addition of plasticizer should be approached with caution so as not to compromise the integrity of the gelatin capsule or cause leakage. In certain compositions it is better not to use plasticizers.

Examples of other additives that may be used as part of the formulations of the invention include, but are not limited to carbohydrates, sugars, sucrose, sorbitol, mannitol, zinc salts, tannic acid salts; salts of acids and bases such as sodium and potassium phosphates, sodium and potassium hydroxide, sodium and potassium carbonates and bicarbonates; acids such as hydrochloric acid, sulfuric acid, nitric acid, and phosphoric acid, citric acid, tartaric acid, and benzoic acid.

Materials such as the alkali metal chlorides, ammonium chloride, and chlorides of Ba, Mg, Ca, Cu, Fe and Al; alkali or alkaline earth solutions of acetates, nitrates, phosphates, and hydroxides may be used in this invention.

Hygroscopic or aqueous materials may be used with caution. Limited quantities have been incorporated in certain compositions. For example, a paste composition may comprise an aqueous vehicle in combination with a non-aqueous vehicle in the presence of an emulsifier.

The composition of the invention comprising one or more active substances may be made by any method wherein the quantity or ratio and type of clays, controlled release agents, oily, fatty or waxy substance and optionally fillers is sufficient to form a paste, liquid or semi solid matrix, magma of the entire composition. Preferably, the entire quantity of the composition is dissolved, dispersed, emulsified or suspended in the oily, fatty or waxy substances. Typically, the clays, controlled release agent and oily, fatty or waxy substances are combined, such as by blending or mixing under high shear until the clays, controlled release agent is completely dissolved, or homogeneous paste is formed. The components may be added separately one after the other. The active substance is added under high shear to form a homogeneous non Newtonian, thixotropic or pseudoplastic paste or liquid/semi solid matrix. The order of incorporation depends on the outcome to be achieved. A cold process under room temperature conditions is preferred, however solid substances may be heated to their liquid state prior to incorporation.

Alternatively, the composition may be processed in a jacketed vessel which allows precise control of the processing temperature. Other pharmaceutically acceptable additives, such as those described above, may be incorporated before, after, or during the addition of controlled release agents or narcotic analgesics.

The manufacture of the composition of this invention is relatively simple. Formulation may be prepared at room temperature. Typically, no heating of the ingredients are required. However, when materials that are solid at room temperature are to be used, heating may be necessary. Solvents having high volatile properties are typically not used. Examples of such volatile solvents are: benzene, toluene, xylene, hexane, cyclohexanole, cyclohexane, methylcyclohexanole, dioxane, ethylacetate, acetone, amylacetate, propylacetate, methylethylketone, ethylcellosolve, isopropylalcohol, methanol, ethylalcohol and isoamylalcohol.

In certain examples solid non-dissolved particles may be dispersed within a paste. The solid particles will be of a size such that the paste composition maintains its consistency/ viscosity and homogeneity at room temperature conditions and during storage. The solid particles may take any convenient form, including, for example, granules, spheroids, pellets, microspheres, nanospheres, microcapsules, or crystals and can be prepared by wet or dry granulation, by extrusion spheronization, by powder or solution layering, by microencapsulation techniques, by milling and compression techniques or other suitable known techniques. In certain examples, different populations of coated particles can be mixed together within a paste composition.

In certain examples, the particle size of solid materials is less than about 1000 microns and the composition maintains its consistency/viscosity and homogeneity at room temperature conditions and during storage. In certain other examples, the particle size of solid materials is less than about 500, 200, 100, or 50 microns and the composition maintains its consistency/viscosity and homogeneity at room temperature conditions and during storage. In certain further, examples the solid particles are efficiently small such that the paste composition is essentially a homogeneous non-Newtonian, thixotropic or pseudoplastic paste.

A singular paste composition may be used or a combination of two or more paste compositions may be used. In certain examples, a single paste composition may comprise one or more active substances. In certain other examples, two or more paste compositions may have different release profiles (for example, controlled release and immediate release) and may comprise the same or different active substance(s). Multiple paste compositions may be useful for delivery of one or more active substances. For example, multiple paste compositions may be useful for delivery of two or more substances that are incompatible or are to act separately or at a different onset of action. If desired, multiple paste compositions may be encapsulated together or delivered together in any other suitable dispensing device.

In certain examples, paste compositions are enveloped by capsules, for example, soft of hard capsules. While both soft and hard capsules may be used, hard capsules may be particularly useful. In certain examples, the capsule is a hard gelatin capsule or is made of a metal or alloy of metals from the periodic table, cellulose ether, vegetable or animal origin.

Capsules are often made from gelatin. Gelatin capsules are traditionally divided into two general groups; hard shell gelatin capsules and soft gelatin capsules (softgels). In certain examples of hard shell gelatin capsules, the capsule is typically in equilibrium with a relative humidity of less than 20%; is typically formulated with a low ratio of dry plasticizer to dry gelatin (low amounts of plasticizer); and is typically made of two separately formed, cooperating, telescoping shells. On the other hand, softgels are most commonly in equilibrium with a relative humidity of between 20% and 30%, are typically formulated with a high ratio of dry plasticizer to dry gelatin (higher amounts of plasticizer); and are typically formed in a unitary process such as a rotary die encapsulation process.

Capsules from materials other than gelatin will also be known to the skilled person. For example, US Patent Appln. Pub. No. 20060099246 (Tanner) published May 11, 2006 pertains to a non-gelatin soft capsule system having a predominantly starch and gelling carrageenan based shell. Carrageenan is a collective term for polysaccharides prepared by alkaline extraction (and modification) from red seaweed (Rhodophycae), mostly of genus *Chondrus, Eucheuma, Gigartina* and *Iridaea*. Different seaweeds produce different carrageenans. Carrageenan consists of alternating 3-linked-beta-D-galactopyranose and 4-linked-alpha-D-galactopyranose units. Most, if not all, of the galactose units are substituted with sulfate ester groups. As another example, US Patent Appln. Pub. No. 20060004193 (Muller) published Jan. 5, 2006 relates to a tough-elastic material based on starch, which on the one hand has high impact toughness at low humidities, and on the other hand still has a high modulus of elasticity at high humidities and has a high elongation capacity in a broad range of humidities and on account of its property profile is suited to use as edible film and for the packaging of active ingredients, as well as high-quality substitution of gelatine in the area of soft and hard capsules. As another example, PCT publication WO 01/37817 describes a soft capsule based on thermoplastic starch (TPS) with high softener content. As another example, US Patent Appln. Pub. No. 20050196436 (Chantranukul) published Sep. 8, 2005, relates to a method of producing a film forming blend of different acyl gellan gums with starch having similar textural and functional properties compared to gelatin. As another example, US Patent Appln. Pub. No. 20070077293 (Park) published Apr. 5, 2007 relates to a film-forming composition for hard capsules, comprising 7-12% by weight of starch, 1-6% by weight of a plasticizer, 0.7-3% by weight of a gelling agent, and 79-91.3% by weight of water. As another example, US Patent Appln. Pub. No. 20060153909 (Motoune) published Jul. 13, 2006, relates to hard capsules made of a base material containing a cellulose derivative including, for example, one or more of hydroxypropyl methylcellulose, methylcellulose, hydroxypropyl cellulose, hydroxyethyl cellulose, hydroxypropyl methylcellulose phthalate, hydroxypropyl methylcellulose acetate succinate, carmelose, carboxymethylethyl cellulose, cellulose acetate phthalate, and ethylcellulose. Also, additives such as a gelling agent, a gelling aid, a colorant, a plasticizer, an emulsifier, a dispersant, and a preservative may be added to the capsule base material. As yet another example, US Patent Appln. Pub. No. 20050186268 (Hoshi) published Aug. 25, 2005, describes a hard capsule made mainly of a polymer or copolymer obtained by polymerizing or copolymerizing at least one polymerizable vinyl monomer in the presence of polyvinyl alcohol and/or a derivative thereof. Still many other examples exist, as will be recognized by the skilled person.

In certain examples, a controlled release composition may be filled into a capsule or dispensing device alone and utilized, or it may be co-filled with non controlled release composition containing opiod antagonist and/or immediate release non narcotic analgesics or other pharmaceutically active substances.

Paste compositions allow for a clean break during formation or dosing ("stringing") into gelatin capsule or device. With regard to two-piece capsules, the paste composition should be of sufficient viscosity to prevent possible splashing of the bushings that may occur and which could contaminate the area of overlap between the capsule body and cap and prevent a good seal from being formed.

Capsules comprising paste compositions may be prepared by any number of known suitable techniques. The fill material used in a capsule generally contains a pharmaceutical dissolved or dispersed in a carrier that is compatible with the capsule wall.

In certain examples, a liquid or semi-solid matrix, magma or paste is filled in a gelatin capsule for which dissolution using a USP dissolution tester is not significantly different by the rotation speed of the basket or paddle in the speed range from about 25 rpm to about 150 rpm, or at about 50 rpm and about 100 rpm or at about 50 rpm and about 75 rpm or at about 100 rpm and about 150 rpm. The rotation speed does not interact with or compromise the integrity of the composition and release mechanism. Compositions that meet these requirements perform consistently in the gastrointestinal tract without fear of collapse or disintegration, They are typically not perturbed, crushed or damaged by gastrointestinal tract content, resident time or motility. These types of composition may be prized for their reliability.

Compositions comprising addictive substances, clays, controlled release agents or oily, waxy or fatty substances are formulated to be compatible with the gelatin capsule shell and not compromise the integrity of the capsule shell.

A gelatin capsule may be coated on the internal and/or external surface of the gelatin capsule in order to control the site and/or rate of delivery of an active substances or protect the composition from environmental factors such as moisture or for aesthetic appeal.

A capsule or other particles may be coated with a polymeric coating. Methods of polymeric coating are well known in the art. For example, a core particle may be coated in a fluidized bed or pan, or by spraying or painting a polymeric coat onto a core particle. Another known option is a fluid bed bottom spray coater by having particles suspended in an air stream, and an aqueous dispersion of a polymeric coating composition is sprayed on to the particles. Various conventional coating apparatuses may be employed to facilitate this including, for example, a centrifugal fluidized bed coating apparatus, a pan coating apparatus, or a fluidized bed granulating coating apparatus.

Water insoluble organosoluble polymers which are used in the present invention may be any polymers which are insoluble in water, are capable of being homogenously dissolved or dispersed in an organosolvent, and can typically retard the release of active ingredients. By the term "water-insoluble" is intended not susceptible to being dissolved (in water). Specific examples of water insoluble organosoluble polymers are, cellulose ether, cellulose ester, or cellulose ether-ester e.g., ethyl cellulose, acetyl cellulose, and nitrocellulose. Other water insoluble organosoluble polymers that can be used include acrylic and/or methacrylic ester polymers, polymers or copolymers of acrylate or methacrylate polyvinyl esters, polyvinyl acetates, polyacrylic acid esters, and butadiene styrene copolymers, and the like. Preferred water insoluble polymers are, ethylcellulose, cellulose acetate, polymethacrylates and aminoalkyl methacrylate copolymer.

In further specific examples, the acrylic polymer, includes, but is not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly (methyl methacrylate), poly(methyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The water insoluble polymers can be used either singly or in combinations of two or more.

Water soluble gel forming polymers which may be used in the present invention may be any polymers which are soluble in water, are capable of being homogenously dissolved or dispersed in an organosolvent, and can typically retard the release of active ingredients. Typically, the water soluble gel forming polymer is capable of hydrating quickly and forming strong, viscous gels. By the term "water-soluble" is intended susceptible of being dissolved (in water). Suitable water soluble gel forming polymers include those which can form hydrocolloid or can form a strong, viscous gel through which an active ingredient is released via diffusion or wicking. They include naturally occurring or synthetic, anionic or nonionic, hydrophilic rubbers, starch derivatives, cellulose derivatives, proteins, and the like. Specific non-limiting examples are gelatin, such as alginates, pectins, carrageenans, or xanthan; cellulose derivatives, such as methyl cellulose, hydroxypropylcellulose, hydroxyethylcellulose, hydroxypropyl methylcellulose, or sodium carboxymethylcellulose; starch and starch derivatives such as alpha starch or sodium carboxymethyl starch; galactomannan and galactomannan derivatives; polyvinylpyrrolidone, polyvinyl alcohol, vinyl-pyrrolidone-vinylacetate-copolymers, acacia, tragacanth, xanthan gum, locust bean gum, guar-gum, karaya gum, pectin, arginic acid, polyethylene oxide, Carbomer, polyethylene glycols, polypropylene glycols, carboxyvinyl polymer, sodium polyacrylate, albumin, dextrin, dextran sulfate, agar, gelatin, casein, sodium casein, pullulan, deacetylated chitosan, polyethyoxazoline, polyethylene oxide, poloxamers and the like. Of these, preferable are hydroxyethyl cellulose, hydroxypropyl methylcellulose, methylcellulose, hydroxypropyl cellulose, carbomer, polyethylene glycol, poloxamers, starch derivatives and polyvinylpyrrolidone. Water soluble gel forming polymers can be used either singly or in combinations of two or more.

Polymeric coats may also be comprised of: hydrophobic or water repellant material such as oils, fats, waxes, higher alcohols; pH sensitive polymers; enteric polymers; or any other polymer, component or material known to be useful for preparing a controlled release coating.

The polymers used in the present invention may be pH insensitive or pH sensitive. For a delivery device designed to be orally administered to the digestive tract, polymers that are known to be orally ingestible can be used and include, for example, polyvinyl alcohol, hydroxypropyl methyl cellulose, and other cellulose-based polymers. Other known polymers useful for enteral delivery include polymer materials which preferentially dissolve or disintegrate at different points in the digestive tract. Such polymers include, for example, the known acrylic and/or methacrylic acid-based polymers which are soluble in intestinal fluids, e.g. the Eudragit™ series of commercially available polymers. Examples of these include Eudragit E™, such as Eudragit E 100™, which preferentially dissolves in the more acid pH of the stomach, or enteric polymers such as Eudragit L™ and/or Eudragit S™ which preferentially dissolve in the more alkaline pH of the intestine, or polymers which dissolve slowly, e.g. a predetermined rate in the digestive tract, such as Eudragit RL™, e.g. Eudragit RL 100™, and/or Eudragit RS™ e.g. Eudragit R 100™, and/or blends of such Eudragit™ polymers.

Hydrophobic or water repellant material that may be present in a coat is chosen from oil and fats, waxes, higher fatty acids, fatty acid esters, higher alcohols, hydrocarbons, and metal salts of higher fatty acids. Specific examples of oils and fats include plant oils, e.g. cacao butter, palm oil, Japan wax (wood wax), coconut oil, etc.; animal oils, e.g. beef tallow, lard, horse fat, mutton tallow, etc.; hydrogenated oils of animal origin, e.g. hydrogenated fish oil, hydrogenated whale oil, hydrogenated beef tallow, etc.; hydrogenated oils of plant origin, e.g. hydrogenated rape seed oil, hydrogenated castor oil, hydrogenated coconut oil, hydrogenated soybean oil, etc.; and the like. Of these hydrogenated oils are preferred as an oil component of the present invention.

Specific examples of waxes include plant waxes, e.g. carnauba wax, candelilla wax, bayberry wax, auricurry wax, espalt wax, etc.; animal waxes, e.g. bees wax, breached bees wax, insect wax, spermaceti, shellac, lanolin, etc; and the like. Of these preferred are carnauba wax, white beeswax and yellow beeswax.

Paraffin, petrolatum, microcrystalline wax, and the like, are given as specific examples of hydrocarbons, with preferable hydrocarbons being paraffin and microcrystalline wax.

Given as examples of higher fatty acids are caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, and the like. Of these, preferable are myristic acid, palmitic acid, stearic acid, and behenic acid.

Specific examples of higher alcohols are lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, corianyl alcohol, ceryl alcohol, and myricyl alcohol. Particularly preferable alcohols are cetyl alcohol, stearyl alcohol, and the like.

Specific examples of esters are fatty acid esters, e.g. myristyl palmitate, stearyl stearate, myristyl myristate, behenyl behenate, ceryl lignocerate, lacceryl cerotate, lacceryl laccerate, etc.; glycerine fatty acid esters, e.g. lauric monoglyceride, myristic monoglyceride, stearic monoglyceride, behenic monoglyceride, oleic monoglyceride, oleic stearic diglyceride, lauric diglyceride, myristic diglyceride, stearic diglyceride, lauric triglyceride, myristic triglyceride, stearic triglyceride, acetylstearic glyceride, hydroxystearic triglyceride, etc.; and the like. Glycerine fatty acid esters are more preferable.

Specific examples of metal salts of higher fatty acid are calcium stearate, magnesium stearate, aluminum stearate, zinc stearate, zinc palmitate, zinc myristate, magnesium myristate, and the like, with preferable higher fatty acid salts being calcium stearate and magnesium stearate.

An polymeric coating composition may also contain other additives normally found in coatings used in the pharmaceutical art such as plasticizers, anti-tacking agents such as talc and coloring agents.

Examples of plasticizers include diethylphthalate, triethyl citrate, triethyl acetyl citrate, triacetin, tributylcitrate, polyethylene glycol, glycerol, vegetable and mineral oils. When using capsules, the addition of plasticizer should be approached with caution so as not to compromise the integrity of the gelatin capsule or cause leakage. In certain compositions it is better not to use plasticizers.

Coloring agents are added for elegance and aesthetics or to differentiate products and may be chosen, for example, from metal oxide pigments or aluminum lake dyes.

A coating composition may include an anti-tacking agent such as talc. Other examples of suitable anti-tacking agent are calcium stearate, colloidal silicon dioxide, glycerin, magnesium stearate, and aluminum stearate.

In a specific example, an polymeric coating is prepared by adding polymers, plasticizer, and anti-tacking agent to an organosolvent and mixed until homogenously dissolved or dispersed using a high shear mixer. The coating may be applied to a core particle using standard coating methodology.

A paste composition of the present invention may be used for treatment of a patient, for example, an animal and more particularly, a mammal. By mammal, is meant any member of the class of mammalia that is characterized by being a vertebrate having hair and mammary glands. Examples include, without limitation, dog, cat, rabbit, horse, pig, goat, cow, human being. The paste composition of the present invention may be administered to any animal patient or mammalian patient that is in need of treatment with a site specific, timed, pulsed, chronotherapeutic, extended, or controlled release of an active ingredient. In one example, a delivery device of the present invention is used for treating a horse. In another example, a delivery device of the present invention is used for treating a human being.

A medical condition or dose dumping may be prevented or treated by administering to a patient a paste composition comprising a therapeutically effective amount of an addictive substance.

In certain examples of methods of preparing or using a paste composition, the administration in man or animal may be internal, such as oral or parenteral. Such internal parenteral administration includes but is not limited to intravascular, intramuscular, subcutaneous, intradermal, intrathecal, and intracavitary routes of administration, as well as application to the external surface of an internal bodily organ, such as during a surgical or laparoscopic procedure. The administration may be topical, including administration to the skin or to a mucosal surface, including the oral, vaginal, rectal surfaces, to the surface of the eye, to the nasal passages, or to the ear canal.

The composition may also be in the form of a solid. The means and area of application will depend on the particular condition that is being treated. The composition may be dispensed using any suitable formulation and/or dispensing device. For example, it may be taken orally, implanted, intravenously or as a depot. It may be targeted at specific sites in the gastrointestinal tract (GU) or to specific organs. As another example, the composition may also be applied buccally and transdermally in a pouch or patch.

The composition may be applied to bodies of water, such as rivers, lakes, or oceans, to the atmosphere, or to land. It is evident that the physical state of the formulation and the particular method of application may vary accordingly.

Solid particles may be prepared by conventional techniques. The preferred technique is by dry or wet granulation of an addictive substance and excipients such as solubilizing agents, emulsifying agents, suspending agents, fillers, compression agents, stabilizers, pH altering agents, buffers, lubricants, and glidants.

Fillers, such as lactose, and compression agents such as microcrystalline cellulose, lubricants such as magnesium stearate and glidants such silicone dioxide may, in certain examples, be included in the core. The core onto which the coating is applied contains the active component. The core may be a tablet, capsule, caplet, pellet, spherical or irregular in shape.

In certain examples, swellable polymeric materials such as hydrogels that swell and expand significantly are included in the core.

Excipients may be homogenously mixed with an active ingredient in a core particle. Excipients may be selected from antiadherents, binders, diluents, emulsifying agents, suspending agents, compression agents, extrusion agents, pH altering agents, buffers, glidants, lubricants, solubilizers, wetting agents, surfactants, penetration enhancers, pigments, colorants, flavoring agents, sweetners, antioxidants, acidulants, stabilizers, antimicrobial preservatives and binders.

Excipients are biologically inert ingredients which enhance the therapeutic effect. The filler or diluent (eg lactose or sorbitol) is a bulking agent, providing a quantity of material which can accurately be formed into a tablet. The binders and adhesives (eg methyl cellulose or gelatin) hold the ingredients together so that they form a tablet and hold together. Lubricants (eg magnesium stearate or polyethylene glycol) are added to improve powder flow so that the die fills accurately, they also reduce the friction between the tablet and the machine so that the process progresses smoothly and uniformly.

Antiadherents are used to reduce the adhesion between the powder (granules) and the punch faces and thus prevent tablet sticking to the punches.

Binders hold the ingredients in a tablet together. Binders ensure that tablets and granules can be formed with required mechanical strength. Binders may be selected from starches, sugars, cellulose or modified cellulose such as hydroxypropyl cellulose, lactose, or sugar alcohols like xylitol, sorbitol or maltitol. Solution binders are dissolved in a solvent (for example water or alcohol and used in wet granulation processes. Examples of solution binders are gelatin, cellulose, cellulose derivatives, polyvinyl pyrrolidone, starch, sucrose and polyethylene glycol. Dry binders are added to a powder blend, either after a wet granulation step, or as part of a direct powder compression. Examples of dry binders are cellulose, methyl cellulose, polyvinyl pyrrolidone, polyethylene glycol. A commonly used binder or compression agent is microcrystalline cellulose. Microcrystalline and powdered cellulose products are sold under the tradenames Avicel™ PH (FMC Corporation, Philadelphia, Pa.) and Solka Floc™ (Penwest Company, Patterson N.Y.). Microcrystalline cellulose may be used in various techniques such as direct compression, dry granulation, wet granulation, or extrusion-spheronization.

Compression agents are materials that may be compacted. Compression agents may be added to increase the overall hardness of a core particle. Compression agents have inherently high compatibility due to properties of plastic deformation and limited elastic recovery. Non-limiting examples of materials that find use as compression agents are microcrystalline cellulose, silicified microcrystalline cellulose (for example Prosolv™ produced by JRS Pharma), oxidized polyethylene, calcium hydrogen phosphate dehydrate, dextrate, or sugar.

Fillers or diluents are added for bulk to fill out the size of a tablet or capsule, making it practical to produce and convenient for the consumer to use. Fillers/diluents are typically inert, compatible with the other components of the formulation, non-hygroscopic, soluble, relatively cheap, compatible, and preferably tasteless or pleasant tasting. Plant cellulose (pure plant filler) is a popular filler in tablets or hard gelatin capsules. Dibasic calcium phosphate is another popular tablet filler. A range of vegetable fats and oils can be used in soft gelatin capsules. Other examples of fillers include: lactose, sucrose, glucose, mannitol, sorbitol, and, calcium carbonate. Fillers/diluents are typically selected from microcrystalline cellulose, plant cellulose, calcium phosphate, mannitol, sorbitol, xylitol, glucitol, ducitol, inositiol, arabinitol; arabitol, galactitol, iditol, allitol, fructose, sorbose, glucose, xylose, trehalose, al lose, dextrose, altrose, gulose, idose, galactose, talose, ribose, arabinose, xylose, lyxose, sucrose, maltose, lactose, lactulose, fucose, rhamnose, melezitose, maltotriose, and raffinose. Preferred sugars include mannitol, lactose, sucrose, sorbitol, trehalose, glucose.

Glidants are used to improve the flowability of the powder or granules or both. Some examples of glidant(s) are silicon dioxide, starch, calcium silicate, Cabosil, Syloid, and silicon dioxide aerogels. Typically, silicon dioxide is used.

Lubricants prevent ingredients from clumping together and from sticking to the tablet punches or capsule filling machine. Lubricants also ensure that tablet formation and injection can occur with low friction between the solid and die wall. Some examples of lubricant(s) are alkali stearates such as magnesium stearate, calcium stearate, zinc stearate, polyethylene glycol, adipic acid, hydrogenated vegetable oils, sodium chloride, sterotex, glycerol monostearate, talc, polyethylene glycol, sodium benzoate, sodium lauryl sulfate, magnesium lauryl sulfate, sodium stearyl fumarate, light mineral oil and the like may be employed. Waxy fatty acid esters, such as glyceryl behenate, sold as "Compritol" products, can be used. Other useful commercial lubricants include "Stear-O-Wet" and "Myvatex TL". Common minerals like talc or silica, and fats, e.g. vegetable stearin, glycerol monostearate, magnesium stearate or stearic acid are typically used lubricants.

Sorbents are used for moisture-proofing by limited fluid sorbing (taking up of a liquid or a gas either by adsorption or by absorption) in a dry state.

Surfactants, wetting agents and solubilisers such as glycerol monostearate, cetostearyl alcohol, cetomacrogol emulsifying wax, sorbitan esters, polyoxyethylene alkyl ethers (e.g., macrogol ethers such as cetomacrogol 1000), polyoxyethlylene castor oil derivatives, polyoxyethylene sorbitan fatty acid esters (e.g., TWEEN™), polyoxyethylene stearates, sodium dodecylsulfate, Tyloxapol (a nonionic liquid polymer of the alkyl aryl polyether alcohol type, also known as superinone or triton) is another useful solubilisers. Most of these solubilisers, wetting agents and surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986).

Preferred wetting agents include tyloxapol, poloxamers such as PLURONIC™ F68, F127, and F108, which are block copolymers of ethylene oxide and propylene oxide, and polyxamines such as TETRONIC™ 908 (also known as POLOXAMINE™ 908), which is a tetrafunctional block copolymer derived from sequential addition of propylene oxide and ethylene oxide to ethylenediamine (available from BASF), dextran, lecithin, dialkylesters of sodium sulfosuccinic acid such as AEROSOL™ OT, which is a dioctyl ester of sodium sulfosuccinic acid (available from American Cyanimid), DUPONOL™ P, which is a sodium lauryl sulfate (available from DuPont), TRITON™ X-200, which is an alkyl aryl polyether sulfonate (available from Rohm and Haas), TWEEN™ 20 and TWEEN™ 80, which are polyoxyethylene sorbitan fatty acid esters (available from ICI Specialty Chemicals), Carbowax 3550 and 934, which are polyethylene glycols (available from Union Carbide), Crodesta F-110, which is a mixture of sucrose stearate and sucrose distearate, and Crodesta SL-40 (both available from Croda Inc.), and SA90HCO, which is $C_{18}H_{37}$—$CH_2$ $(CON(CH_3)CH_2(CHOH))_4$ $CF_2OH)_2$.

Wetting agents which have been found to be particularly useful include Tetronic 908, the Tweens, Pluronic F-68 and polyvinylpyrrolidone. Other useful wetting agents include decanoyl-N-methylglucamide; n-decyl-.beta.-D-glucopyranoside; n-decyl-.beta.-D-maltopyranoside; n-dodecyl-.beta.-D-glucopyranoside; n-dodecyl.beta.-D-maltoside; heptanoyl-N-methylglucamide; n-heptyl-.beta.-D-glucopyranoside; n-heptyl-.beta.-D-thioglucoside; n-hexyl-.beta.-D-glucopyranoside; nonanoyl-N-methylglucamide; n-octyl-.beta.-D-glucopyranoside; octanoyl-N-methylglucamide; n-octyl-.beta.-D-glucopyranoside; and octyl-.beta.-D-thioglucopyranoside. Another preferred wetting agent is p-isononylphenoxypoly(glycidol), also known as Olin-10G or Surfactant 10-G (commercially available as 10G from Olin Chemicals). Two or more wetting agents can be used in combination.

The pharmaceutical composition or device may further include a pegylated excipient. Such pegylated excipients include, but are not limited to, pegylated phospholipids, pegylated proteins, pegylated peptides, pegylated sugars, pegylated polysaccharides, pegylated block-co-polymers with one of the blocks being PEG, and pegylated hydrophobic compounds such as pegylated cholesterol. Representative examples of pegylated phospholipids include 1,2-diacyl 1-sn-glycero-3-phosphoethanolamine-N-[Poly (ethylene glycol) 2000] ("PEG 2000 PE") and 1,2-diacyl-sn-glycero-3-phosphoethanolamine-N-[Poly(ethylene glycol) 5000]("PEG 5000 PE"), where the acyl group is selected, for example, from dimyristoyl, dipalmitoyl, distearoyl, diolcoyl, and 1-palmitoyl-2-oleoyl.

Additional excipients may be included in the composition of the present invention. Further examples of excipients can include pigments, colorants, flavoring agents, preservatives and sweeteners. Flavors and colors are added to improve the taste or appearance of a formulation. Some typical preservatives used in pharmaceutical formulations are antioxidants such as vitamin A, vitamin E, vitamin C, and selenium, amino acids such as cysteine and methionine, citric acid and sodium citrate, or synthetic preservatives such as methyl paraben and propyl paraben. Sweeteners are added to make the ingredients more palatable, especially in chewable tablets such as antacid or liquids like cough syrup. Sugar may be used to disguise unpleasant tastes or smells.

One skilled in the art can select appropriate excipients for use in the composition of the present invention.

The paste composition may comprise an excipient that is a swellable material such as a hydrogel in amounts that can swell and expand. Examples of swellable materials include hydrophilic polymers that are lightly cross-linked, such cross-links being formed by covalent or ionic bond, which interact with water and aqueous biological fluids and swell or expand to some equilibrium state. Swellable materials such as hydrogels exhibit the ability to swell in water and retain a significant fraction of water within its structure, and when cross-linked they will not dissolve in the water. Swellable polymers can swell or expand to a very high degree, exhibiting a 2 to 50 fold volume increase. Specific examples of hydrophilic polymeric materials include poly (hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like. Other examples of swellable materials include hydrogels exhibiting a cross-linking of 0.05 to 60%, hydrophilic hydrogels known as Carbopol™ acidic carboxy polymer, Cyanamer™ polyacrylamides, cross-linked water-swellable indene-maleic anhydride polymers, Good-rite™ polyacrylic acid, polyethyleneoxide, starch graft copolymers, Aqua-Keeps™ acrylate polymer, diester cross-linked polyglucan, and the like. Methods for testing swellable materials with regards to polymer imbibition pressure and hydrogel-water interface interaction are described in U.S. Pat. No. 4,327,725 issued May 4, 1982, titled "Osmotic device with hydrogel driving member".

In a certain example, the device may be coated with a non-disintegrating and non-semi-permeable coat. Materials useful for forming the non-disintegrating non-semi-permeable coat are ethylcellulose, polymethylmethacrylates, methacrylic acid copolymers and mixtures thereof.

In yet another embodiment, the device is coated with a non-disintegrating semipermeable coat. Materials useful for forming the non-disintegrating semipermeable coat are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,612,008. The most preferred non-disintegrating semipermeable coating material is cellulose acetate comprising an acetyl content of 39.3 to 40.3%, commercially available from Eastman Fine Chemicals.

In an alternative embodiment, the non-disintegrating semipermeable or non-disintegrating non-semi-permeable coat can be formed from the above-described polymers and materials that will form pores or channels in the coat. The pore forming agents or channeling agents dissolve on contact with fluid and form passages through which fluid and active pharmaceutical ingredient(s) can move through the coat. The pore forming agent or channeling agent can be a water soluble material or an enteric material. Some general examples of pore forming agents or channeling agents are watersoluble materials such as cellulose ethers, polyethylene glycols or microcrystalline cellulose. Some further examples of pore forming agents or channeling agents are sodium chloride, potassium chloride, lactose, sucrose, sorbitol, mannitol, polyethylene glycol (PEG), for example PEG 600, polyvinyl pyrolidone, propylene glycol, hydroxypropyl cellulose, hydroxypropyl methylcellulose, hydroxypropyl methycellulose phthalate, cellulose acetate phthalate, polyvinyl alcohols, methacrylic acid copolymers and mixtures thereof.

The active pharmaceutical ingredient(s) that are water soluble or that are soluble under intestinal conditions may also be used to create pores in the coat.

The pore forming agent comprises approximately 0 to about 75% of the total weight of the coating, most preferably about 0.5% to about 25% of the total weight of the coating. The pore forming agent dissolves or leaches from the coat to form pores in the coat for the fluid to enter the core and dissolve the active ingredient.

As used herein the term pore includes an aperture, orifice, bore, channel, hole, a discrete area of weakness or as created by soluble or leachable materials.

Certain general illustrative examples of paste compositions and their uses may be helpful in understanding the present invention and are itemized as follows:

Item 1 is a timed, delayed or extended release liquid or semi-solid matrix or magma or paste composition which is non-newtonian and composed of one or more addictive substances and,
  (i) one or more clays,
  (ii) and/or one or more substances selected from polyacrylates, starches, carbomers, cellulose ethers, cellulose esters, polysaccharide gums, natural gums, fillers and poloxamers
  (iii) admixed in oily, waxy or fatty substance or a combination thereof
  (iv) and particle size of non dissolved materials is less than 1000 microns
  (v) and administered in a capsule or dispensing device Item 2 is a timed, delayed or extended release liquid or semi-solid matrix or magma or paste composition which is non-newtonian and composed of one or more addictive substances and,
  (i) one or more clays,
  (ii) and/or one or more substances selected from polyacrylates, starches, carbomers, cellulose ethers, cellulose esters, polysaccharide gums, natural gums, fillers and poloxamers
  (iii) admixed in an aqueous vehicle
  (iv) and particle size of non dissolved materials is less than 1000 microns
  (v) and administered in a capsule or dispensing device.

Item 3 is a timed, delayed or extended release liquid or semi-solid matrix or magma or paste composition which is non-newtonian and composed of one or more addictive substances and,
  (i) one or more clays,
  (ii) and/or one or more substances selected from polyacrylates, starches, carbomers, cellulose ethers, cellulose esters, polysaccharide gums, natural gums, fillers and poloxamers
  (iii) admixed in a vehicle which is made by combining water and one or more of oily, waxy and fatty substance
  (iv) and particle size of non dissolved materials is less than 1000 microns
  (v) and administered in a capsule or dispensing device Item 4 is the composition according to items 1, 2 or 3 which contains one or more surfactant.

Item 5 is the composition according to items 1, 2 or 3 which contains one or more disintegrants.

Item 6 is the composition according to items 1, 2 or 3 which contains one or more medium chain triglycerides or their esters.

Item 7 is the composition according to items 1, 2 or 3 which contains d-alpha-tocopheryl polyethylene glycol 1000 succinate and or glyceryl monostearate and or soy polysaccharides.

Item 8 is the composition according to items 1, 2 or 3 in which the clay is bentonite.

Item 9 is the composition according to items 1, 2 or 3 in which the clay is montmorillonite.

Item 10 is the composition according to items 1, 2 or 3 in which the clay is Pascalite. Item 11 is the composition according to items 1, 2 or 3 in which the clay is Smectite, illite, sepiolite, palygorskite, muscovite, amesite, hectorite, fluorohectorite, saponite, beidellite, talc, nontronite, stevensite, mica, vermiculite, fluorovermiculite, halloysite and fluorine-containing synthetic types of mica, phyllosilicates, beidellite; volkonskoite; hectorite; sauconite; sobockite; svinfordite; and the like, mixed illite/smectite minerals, such as rectorite, tarosovite, ledikite and admixtures of illites with the clay minerals named above.

Item 12 is the composition according to items 1, 2 or 3 which contains one or more stabilizer.

Item 13 is the composition according to items 1, 2 or 3 which contains one or more anti-oxidant.

Item 14 is the composition according to items 1, 2 or 3 which contains one or more anti-foaming substance.

Item 15 is the composition according to items 1, 2 or 3 which contains inorganic or organic bases.

Item 16 is the composition according to items 1, 2 or 3 which contains salts or electrolytes.

Item 17 is the composition according to items 1, 2 or 3 in which the clay is less than 95% by weight.

Item 18 is the composition according to items 1, 2 or 3 in which the clay is less than 5% by weight.

Item 19 is the composition according to items 1, 2 or 3 in which the clay is from about 5% to about 20% by weight.

Item 20 is the composition according to items 1, 2 or 3 in which the clay is from about 20% to about 40% by weight.

Item 21 is the composition according to items 1, 2 or 3 in which the clay is from about 30% to about 60% by weight.

Item 22 is the composition according to items 1, 2 or 3 in which the internal and or external surface of the capsule is coated with a pH sensitive film coat.

Item 23 is the composition according to items 1, 2 or 3 in which the internal and or external surface of the capsule is coated with a non pH sensitive film coat.

Item 24 is the composition according to items 1, 2 or 3 in which the capsule is a hard gelatin capsule or is made of a metal or alloy of metals from the periodic table, cellulose ether, vegetable or animal origin.

Item 25 is a liquid or semi-solid, matrix or magma or paste composition which is non-newtonian, thixotropic and/or pseudoplastic and contains one or more clays or one or more controlled release polymeric agent for timed or extended release of addictive substances.

Item 26 is the composition according to item 25 which contains one or more surfactants.

Item 27 is the composition according to item 25 which contains one or more super disintegrants.

Item 28 is the composition according to item 25 which contains one or more medium chain triglycerides or their esters.

Item 29 is the composition according to item 25 which contains d-alpha-tocopheryl polyethylene glycol 1000 succinate and or glyceryl monostearate and or soy polysaccharides.

Item 30 is the composition according to item 25 in which the clay is bentonite.

Item 31 is the composition according to item 25 in which the clay is a montmorillonite.

Item 32 is the composition according to item 25 in which the clay is Pascalite.

Item 33 is the composition according to item 25 in which the clay is Smectite, illite, sepiolite, palygorskite, muscovite, allevardite, amesite, hectorite, fluorohectorite, saponite, beidellite, talc, nontronite, stevensite, mica, vermiculite, fluorovermiculite, halloysite and fluorine-containing synthetic types of mica, phyllosilicates, beidellite; volkonskoite; hectorite; sauconite; sobockite; svinfordite; and the like, mixed illite/smectite minerals, such as rectorite, tarosovite, ledikite and admixtures of illites with the clay minerals named above.

Item 34 is the composition according to item 25 which contains one or more stabilizer.

Item 35 is the composition according to item 25 which contains one or more anti-oxidant.

Item 36 is the composition according to item 25 which contains one or more anti-foaming substance.

Item 37 is the composition according to item 25 which contains inorganic or organic bases.

Item 38 is the composition according to items 1, 2, 3 or 25 which makes it harder to abuse addictive substances.

Item 39 is the composition according to items 1, 2, 3 or 25 which discourages drug abuse by at least one of the modes of crushing, milling or grinding the dosage form to powder and snorting or inhalation by the nasal route or dissolving for abuse via the parenteral route.

Item 40 is the composition of items 1, 2, 3, or 25 which contains materials selected from ethylene-vinyl acetate polymers, carbomers, cellulose ethers, esters, stearates, cellulose derivatives, acyl substituted cellulose acetates and derivatives thereof, polyurethanes, polystyrenes, polyvinyl chloride, polyvinyl fluoride, poly(vinyl imidazole), chlorosulphonated polyolefins, and polyethylene oxide, polyethylene, polyvinyl pyrrolidone, ethylene vinylacetate, polyethylene glycol, cellulose acetate butyrate and cellulose acetate propionate.

Item 41 is the composition of items 1, 2, 3, or 25 which contains sucrose acetate isobutyrate.

Item 42 is the composition according to item 25 in which the internal and/or external surface of the capsule is coated with a pH sensitive film coat.

Item 43 is the composition according to item 25 in which the internal and/or external surface of the capsule is coated with a non pH sensitive film coat.

Item 44 is the composition according to items 1, 2, 3, or 25 wherein the addictive substance is a drug, prodrug or their salts, bases, intermediates, enantiomers, polymorphs, derivatives, and metabolites or a combination thereof.

Item 45 is the composition according to items 1, 2, 3, or 25 wherein the addictive substance is a narcotic analgesic.

Item 46 is the composition according to items 1, 2, 3, or 25 which contains a poly(lactide).

Item 47 is the composition according to items 1, 2, 3, or 25 which contains a poly(lactide-coglycolide).

Item 48 is the composition of items 1, 2, 3, or 25 which contains a poly(glycolide).

Item 49 is the composition of items 1, 2, 3, or 25 which contains a poly(caprolactone).

Item 50 is the composition of items 1, 2, 3, or 25 which contains an oxidized cellulose.

Item 51 is the composition of items 1, 2, 3, or 25 which contains a poly(D,L-lactic acid).

Item 52 is the composition of items 1, 2, 3, or 25 which contains a nonbiodegradable polymer.

Item 53 is the composition of items 1, 2, 3, or 25 which contains a biodegradable polymer.

Item 54 is the composition of items 1, 2, 3, or 25 suitable for rectal administration.

Item 55 is the composition of items 1, 2, 3, or 25 suitable for oral administration.

Item 56 is a method for the administration of the composition of items 1, 2, 3, or 25, comprising the steps of
(a) providing an amount of controlled release compositions having different release rates; and
(b) administering the compositions to the host in a capsule or patch.

Item 57 is a method for the administration of the composition of items 1, 2, 3, or 25, comprising the step of administering the composition to the host topically on the skin.

Item 58 is a method for the administration of the composition of items 1, 2, 3, or 25, comprising the step of administering the composition to the host via injection.

Item 59 is a method for the administration of the composition of items 1, 2, 3, or 25, comprising the steps of
(a) providing an amount of a controlled release composition and another amount of a composition having different release rates; and
(b) administering the compositions to the host in a capsule or patch.

Item 60 is a method for the administration of the composition of items 1, 2, 3, or 25, comprising the steps of
(a) providing an amount of a controlled release composition and another amount of an immediate release composition; and
(b) administering the compositions to the host in a capsule or patch.

Item 61 is a method for the administration of the composition of items 1, 2, 3, or 25, comprising the steps of
(a) providing an amount of a controlled release composition and another amount of a composition a having different release rates; and
(b) administering the compositions to the host in the same capsule or patch.

Item 62 is a method for the administration of the composition of items 1, 2, 3, or 25, comprising the steps of
(a) providing an amount of a controlled release composition and another amount of a immediate release composition; and
(b) administering the compositions to the host in the same capsule or patch.

Item 63 is a method for the administration of the composition of items 1, 2, 3, or 25, comprising the steps of
(a) providing an amount of a controlled release composition and another amount of a composition having different release rates; and
(b) administering the compositions to the host in the same capsule or patch;
(c) wherein the two compositions contain the same or different drugs.

Item 64 is a method for the administration of the composition of items 1, 2, 3, or 25, comprising the steps of
(a) providing an amount of a controlled release composition and another amount of a immediate release composition; and
(b) administering the compositions to the host in the same capsule or patch;
(c) wherein the two compositions contain the same or different drugs.

Item 65 is a method for the administration of the composition of items 1, 2, 3, or 25, comprising the steps of
(a) providing an amount of a controlled release composition and another amount of a composition having different release rates; and
(b) administering the compositions to the host in the same capsule or patch;
(c) wherein one composition contain an opiod drug and the other a non opiod drug.

Item 66 is a method for the administration of the composition of items 1, 2, 3, or 25, comprising the steps of
(a) providing an amount of a controlled release composition and another amount of a immediate release composition; and
(b) administering the compositions to the host in the same capsule or patch;
(c) wherein one composition contain an opiod drug and the other a non opiod drug.

Item 67 is the composition of items 1, 2, 3, or 25, wherein the composition is prepared without having to go through a heating process.

Item 68 is the composition of items 1, 2, 3, or 25, wherein the composition is encapsulated within a microsphere or microcapsule.

Item 69 is the composition of items 1, 2, 3, or 25, wherein the composition is lyophilized.

Item 70 is the composition of items 1, 2, 3, or 25, wherein the controlled release formulation is associated with inert pharmaceutical excipients, said excipients optionally processed into spheres or other shapes and incorporated into a dosage form.

Item 71 is the method for the administration of the composition of items 1, 2, 3, or 25, comprising the steps of
(a) providing an amount of a controlled release composition and another amount of a composition having different release rates; and
(b) administering the compositions to the host in the same capsule or patch;
(c) wherein one composition contain an opiod agonist and the other a opiod antagonist.

Item 72 is the composition of items 1, 2, 3, or 25 which contains sweetening agents.

Item 73 is the composition of items 1, 2, 3, or 25 which contains coloring agents.

Item 74 is the composition of items 1, 2, 3, or 25, administered for pediatric use.

Item 75 is the composition of items 1, 2, 3, or 25 which is dried.

Item 76 is the composition of items 1, 2, 3, or 25 wherein the addictive substance is an opioid agonist selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, alphaprodine, dextroporpoxyphene, propiram, profadol, phenampromide, thiambutene, pholcodeine, 3-trans-dimethylamino-4-phenyl-4-trans-carbethoxy-delta'-cyclohexene, 3-dimethyl-amino-O-(4-methoxyphenylcarbamoyl)-propiophenone oxime, (−).beta.-2'-hydroxy-2,9-dimethyl-5-phenyl-6,7-benzomorphan, (−)2'-hydroxy-2-(3-methyl-2-butenyl)-9-methyl-5-phenyl-6,7-benzomorphan, pirinitramide, (−).alpha.-5,9-diethyl-2'-hydroxy-2-methyl-6,7-benzomorphan, ethyl 1-(2-dimethylaminoethyl)-4,5,6,7-tetrahydro-3-methyl-4-oxo-6-phenylindole-2-carboxylate, 1-Benzoylmethyl-2,3-dimethyl-3-(m-hydroxyphenyl)-piperidine, N-allyl-7.alpha.-(1-(R)-hydroxy-1-methylbutyl)-6,14-endo-ethanotetrahydro-nororipavine, (−)T-hydroxy-2-methyl-6,7-benzomorphan, noracylmethadol, phenoperidine, .alpha.-dl-methadol, beta.-dl-methadol, .alpha.-1-methadol (2-15 mg.), .beta.-dl-acetylmethadol, alpha.-1-acetylmethadol and .beta.-1-acetylmethadol; or pharmaceutically acceptable salts thereof, stereoisomers thereof, ethers thereof, esters thereof, or mixtures thereof.

Item 77 is the composition according to items 1, 2, 3 or 25 wherein the composition is prepared by blending or homogenizing the components in the composition into a uniform non setting paste in a non-volatile vehicle.

Item 78 is a liquid or semi-solid matrix or magma or paste composition, composed of one or more controlled release agent, and/or one or more clays such as bentonite and one or more addictive substance in a non aqueous vehicle, selected from waxes, Arachis oil, Castor oil, Cottonseed oil, Maize (corn) oil, Olive oil, palm oil, Sesame oil, Soybean oil and Sunflower oil and optionally materials selected from disintegrants, semi-solid or solid lipophilic vehicles, adsorption enhancers humectants, surfactants and stabilizers; wherein the physicochemical properties of the composition makes it harder to abuse the addictive substance and discourages drug abuse by at least one of the modes of crushing, milling or grinding the dosage form to powder or heating the dosage form to vapour and snorting or inhalation by the nasal route or dissolving to abuse via the parenteral route.

Item 79 is a liquid or semi-solid matrix or magma or paste composition, composed of one or more controlled release agent and one or more addictive substance in a non aqueous vehicle, selected from waxes, Arachis oil, Castor oil, Cottonseed oil, Maize (corn) oil, Olive oil, palm oil, Sesame oil, Soybean oil and Sunflower oil and optionally materials selected from disintegrants, semi-solid or solid lipophilic vehicles, adsorption enhancers humectants, surfactants and stabilizers encapsulated in a gelatin capsule which is coated with a delayed release or controlled release film coat; wherein the physicochemical properties of the composition makes it harder to abuse the addictive substance and discourages drug abuse by at least one of the modes of crushing, milling or grinding the dosage form to powder or heating the dosage form to vapour and snorting or inhalation by the nasal route or dissolving to abuse via the parenteral route.

Item 80 is the composition of items 1, 2, 3, 25, 78, or 79 which allows once daily dosing of the narcotic analgesic.

Item 81 is the composition of items 1, 2, 3, 25, 78, or 79 which allows for peak plasma concentration(s) to occur between 3 to 14 hours after dosing of the narcotic analgesic.

Item 82 is the composition of items 1, 2, 3, 25, 78, or 79 which in the presence of alcohol does not dose dump.

Item 83 is the composition of items 1, 2, 3, 25, 78, or 79 which is coated with a film coat and wherein in the presence of alcohol does not dose dump.

Item 84 is the composition of items 1, 2, 3, 25, 78, or 79 which is coated with a film coat containing cellulose esters or polymethacrylates or polyethylene glycol or cellulose ethers, esters or a combination wherein in the presence of alcohol does not dose dump.

Item 85 is a liquid or semi-solid matrix or magma or paste composition, composed of one or more controlled release agent and one or more addictive substance which is coated with polymeric and or non polymeric materials selected from a pH sensitive or non pH sensitive or semi-permeable polymers or a combination wherein in the presence of alcohol does not dose dump.

Item 86 is a method for the administration of the composition of items 1, 2, 3, 25, 78, or 79 comprising the steps of
(a) providing an amount of a controlled release composition and another amount of a composition having different release rates; and (b) administering the compositions to the host in a capsule or patch;
(c) in which there is no dose dumping in the presence of alcohol Item 87 is a method for the administration of the composition of items 1, 2, 3, 25, 78, or 79 comprising the steps of
(a) providing an amount of a controlled release composition and another amount of an immediate release composition; and
(b) administering the compositions to the host in a capsule or patch;
(c) in which there is no dose dumping in the presence of alcohol Item 88 is a method for the administration of the composition of items 1, 2, 3, 25, 78, or 79 comprising the steps of
(a) providing an amount of a controlled release composition and another amount of a composition a having different release rates; and
(b) administering the compositions to the host in the same capsule or patch;
(c) in which there is no dose dumping in the presence of alcohol Item 89 is a method for the administration of the composition of items 1, 2, 3, 25, 78, or 79 comprising the steps of
(a) providing an amount of a controlled release composition and another amount of a immediate release composition; and
(b) administering the compositions to the host in the same capsule or patch;
(c) in which there is no dose dumping in the presence of alcohol.

Item 90 is a method for the administration of the composition of items 1, 2, 3, 25, 78, or 79 comprising the steps of
(a) providing an amount of a controlled release composition and another amount of a composition having different release rates; and
(b) administering the compositions to the host in the same capsule or patch;
(c) wherein the two compositions contain the same or different drugs; and
(d) there is no dose dumping in the presence of alcohol Item 91 is a method for the administration of the composition of items 1, 2, 3, 25, 78, or 79 comprising the steps of
(a) providing an amount of a controlled release composition and another amount of a immediate release composition; and
(b) administering the compositions to the host in the same capsule or patch;
(c) wherein the two compositions contain the same or different drugs; and
(d) in which there is no dose dumping in the presence of alcohol Item 92 is a method for the administration of the composition of items 1, 2, 3, 25, 78, or 79 comprising the steps of
(a) providing an amount of a controlled release composition and another amount of a composition having different release rates; and
(b) administering the compositions to the host in the same capsule or patch;
(c) wherein one composition contain an opiod drug and the other a non opiod drug; and
(d) in which there is no dose dumping in the presence of alcohol Item 93 is a method for the administration of the composition of items 1, 2, 3, 25, 78, or 79 comprising the steps of
(a) providing an amount of a controlled release composition and another amount of a immediate release composition; and
(b) administering the compositions to the host in the same capsule or patch;
(c) wherein one composition contain an opiod drug and the other a non opiod drug; and
(d) in which there is no dose dumping in the presence of alcohol Item 94 is a paste composition comprising an addictive substance and a nasal irritants.

Item 95 is a paste composition comprising a pharmaceutical active substance and one or more materials selected from the group consisting of clays, controlled release agents, oily, waxy, and fatty substances for preventing dose dumping in the presence of alcohol.

Item 96 is the composition of items 1, 2, 3, 25, 78, or 79 which provides zero order release, first order or pseudo-first order release of drug content.

Item 97 is the composition of items 1, 2, 3, 25, 78, or 79 which releases less than 60% of drug in 1 hour using USP basket dissolution apparatus 50 rpm.

Item 98 is the composition of items 1, 2, 3, 25, 78, or 79 which releases less than 40% of drug in 1 hour using USP basket dissolution apparatus 50 rpm.

Item 99 is the composition of items 1, 2, 3, 25, 78, or 79 which releases less than 20% of drug in 1 hour using USP basket dissolution apparatus at 50 rpm.

Item 100 is the composition of items 1, 2, 3, 25, 78, or 79 which provides pulsed delivery.

Item 101 is the composition of items 1, 2, 3, 25, 78, or 79 which provides chronotherapeutic delivery.

Item 102 is a composition comprising an active substance and materials selected from the group clays, controlled release agents, oily, waxy, and fatty substances for preventing dose dumping in the presence of alcohol and which makes it difficult for drug abuse.

Item 103 is a composition comprising an active substances in oily, waxy, and fatty substances and optionally materials selected from the group clays, controlled release agents for preventing dose dumping in the presence of alcohol and or which makes it difficult for drug abuse.

Item 104 is the composition according to items 1, 2, 3, 25, 77, 78, 79, 95, 102 or 103 which is presented as tablet, pellet, bead, microsphere, nanoparticle or granules.

Item 105 is the composition according to items 1, 2, 3, 25, 78, 79, 95, 102 or 103 for pediatric use.

Item 106 is the composition according to items 1, 2, 3, 25, 78, 79, 95, 102 or 103 for use as an implant or subcutaneous application.

Item 107 is the composition according to items 1, 2, 3, 25, 78, 79, 95, 102 or 103 wherein dissolution using a USP dissolution tester is not significantly affected by the rotation speed of the basket or paddle in the speed range from about 25 rpm to about 150 rpm.

Item 108 is the composition according to items 1, 2, 3, 25, 78, 79, 95, 102 or 103 wherein dissolution using a USP dissolution tester is not significantly affected by the rotation speed of the basket or paddle in the speed range from about 50 rpm to about 150 rpm.

Item 109 is the composition according to items 1, 2, 3, 25, 78, 79, 95, 102 or 103 wherein dissolution using a USP dissolution tester is not significantly affected by the rotation speed of the basket or paddle in the speed range from about 50 rpm to about 100 rpm.

Item 110 is the composition according to items 1, 2, 3, 25, 78, 79, 95, 102 or 103 wherein dissolution using a USP dissolution tester is not significantly affected by the rotation speed of the basket or paddle in the speed range from about 50 rpm to about 75 rpm.

Item 111 is the composition according to items 1, 2, 3, 25, 78, 79, 95, 102 or 103 wherein there is no dose dumping during dissolution using a USP dissolution tester with basket or paddle assembly in alcoholic media.

Item 112 is the composition according to items 1, 2, 3, 25, 78, 79, 95, 102 or 103 wherein there is no dose dumping during dissolution using a USP dissolution tester with basket or paddle assembly at 50 rpm in about 1% to about 10% alcoholic media.

Item 113 is the composition according to items 1, 2, 3, 25, 78, 79, 95, 102 or 103 wherein there is no dose dumping during dissolution using a USP dissolution tester with basket or paddle assembly at 50 rpm in about 10% to about 20% alcoholic media.

Item 114 is the composition according to items 1, 2, 3, 25, 78, 79, 95, 102 or 103 wherein there is no dose dumping during dissolution using a USP dissolution tester with basket or paddle assembly at 50 rpm in about 20% to about 30% alcoholic media.

Item 115 is the composition according to items 1, 2, 3, 25, 78, 79, 95, 102 or 103 wherein there is no dose dumping during dissolution using a USP dissolution tester with basket or paddle assembly at 50 rpm in about 30% to about 40% alcoholic media.

Item 116 is the composition according to items 1, 2, 3, 25, 78, 79, 95, 102 or 103 wherein there is no dose dumping during dissolution using a USP dissolution tester with basket or paddle assembly at 50 rpm in about 40% to about 50% alcoholic media.

Item 117 is the composition according to items 1, 2, 3, 25, 78, 79, 95, 102 or 103 wherein there is no dose dumping during dissolution using a USP dissolution tester with basket or paddle assembly at 50 rpm in about 50% to about 70% alcoholic media.

Item 118 is the composition according to items 1, 2, 3, 25, 78, or 79, wherein the addictive substance is an opiod agonist or narcotic analgesic or abuse-able substance or euphoric analgesic.

Item 119 is the composition according to items 95, 102, or 103, wherein the active substance is susceptible to abuse or is known to be addictive.

Item 120 is a use of the composition of any one of items 1, 2, 3, 25, 78, or 79 for treatment of addiction to an addictive substance.

Item 121 is a use of the composition of any one of items 1, 2, 3, 25, 78, or 79 for reducing dose dumping of the addictive substance.

Item 122 is a use of the composition of any one of items 1, 2, 3, 25, 78, or 79 for reducing the abuse potential of the addictive substance for at least one of the modes of crushing, milling or grinding the dosage form to powder and snorting or inhalation by the nasal route or dissolving for abuse via the parenteral route.

Item 123 is a method for reducing abuse of an addictive substance by a subject in need of treatment by the addictive substance comprising, administering the composition of any one of items 1, 2, 3, 25, 78, or 79, comprising a therapeutically effective amount of the addictive substance, to the subject.

Item 124 is the method of item 61, wherein the abuse comprises dose dumping.

Item 125 is a method for treating addiction to an addictive substance in a subject comprising, administering the composition of any one of items 1, 2, 3, 25, 78, or 79, comprising a therapeutically effective amount of the addictive substance or a derivative thereof, to the subject.

Item 126 is the method of items 65, 66, or 71 where the opioid agonist is selected from the group consisting of alfentanil, allyiprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, alphaprodine, dextroporpoxyphene, propiram, profadol, phenampromide, thiambutene, pholcodeine, 3-trans-dimethylamino-4-phenyl-4-trans-carbethoxy-delta'-cyclohexene, 3-dimethylamino-O-(4-methoxyphenyl-carbamoyl)-propiophenone oxime, (–).beta.-2'-hydroxy-2,9-dimethyl-5-phenyl-6,7-benzomorphan, (–)2'-hydroxy-2-(3-methyl-2-butenyl)-9-methyl-5-phenyl-6,7-benzomorphan, pirinitramide, (–).alpha.-5,9-diethyl-2'-hydroxy-2-methyl-6, 7-benzomorphan, ethyl 1-(2-dimethylaminoethyl)-4, 5,6,7-tetrahydro-3-methyl-4-oxo-6-phenylindole- -2-carboxylate, 1-Benzoylmethyl-2,3-dimethyl-3-(m-hydroxyphenyl)-piperidine, N-allyl-7.alpha.-(1-(R)-hydroxy-1-methylbutyl)-6,14-endo-ethanotetrahydro-nororipavine, (–)T-hydroxy-2-methyl-6,7-benzomorphan, noracylmethadol, phenoperidine, .alpha.-dl-methadol, .beta.-dl-methadol, .alpha.-1-methadol (2-15 mg.), .beta.-dl-acetylmethadol, alpha.-1-acetylmethadol and .beta.-1-acetylmethadol; or pharmaceutically acceptable salts thereof, stereoisomers thereof, ethers thereof, esters thereof, or mixtures thereof.

When introducing elements disclosed herein, the articles "a", "an", "the", and "said" are intended to mean that there are one or more of the elements unless the context dictates otherwise. For example, the term "a compound" and "at least one compound" may include a plurality of compounds, including mixtures thereof. The terms "comprising", "having", "including" are intended to be open-ended and mean that there may be additional elements other than the listed elements.

The above disclosure generally describes the present invention. A more complete understanding can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Extended Release Oxycodone (Abuse Prevention Capsules)

| Component | Amount (% w/w) |
| --- | --- |
| Oxycodone | 20 |
| Corn Oil | 50 |
| Carbopol 971 | 8 |
| Hydroxypropylmethyl cellulose (METHOCEL ™ KlOOM Premium) | 22 |

The samples were prepared:
1. Weigh corn oil in a glass beaker and immerse Silverson high shear mixer fitted with a homogenizing head into the oil.
2. Gradually add carbopol followed by hydroxypropylmethyl cellulose while stirring vigorously until a homogeneous blend is observed.
3. Add oxycodone gradually while stirring vigorously until a homogeneous blend is observed.
4. The result is a semi-solid or paste which can be filled into hard gelatin capsules without "stringing".
5. Take samples from top, middle and bottom to determine potency and homogeneity of the mix.
6. Fill into hard gelatin capsules.
7. Capsules are tested in a dissolution apparatus in varying concentrations of alcohol with results shown in FIG. 1. Method: 50 rpm, 10 mm cell, paddle/JP sinker wavelength 280 nm. Medium: DI Water or Alcohol and DI Water. Run Mode: 24 hours, sampling every hour.

Example 2

Extended Release Oxycodone (Abuse Prevention Capsules)

| Component | Amount (% w/w) |
| --- | --- |
| Oxycodone | 20 |
| Corn Oil | 49 |
| Carbopol 971 | 8 |
| Bentonite | 1 |
| Hydroxypropylmethyl cellulose (METHOCEL ™ K100M Premium) | 22 |

The samples were prepared:
1. Weigh corn oil in a glass beaker and immerse Silverson high shear mixer fitted with a homogenizing head into the oil.
2. Gradually add bentonite, carbopol and hydroxypropylmethyl cellulose while stirring vigorously until a homogeneous blend is observed.
3. Add oxycodone gradually while stirring vigorously until a homogeneous blend is observed.
4. The result is a semi-solid or paste which can be filled into hard gelatin capsules without "stringing".
5. Take samples from top, middle and bottom to determine potency and homogeneity of the mix.
6. Fill into hard gelatin capsules.

Example 3

Extended Release Oxycodone (Abuse Prevention Capsules)

| Component | Amount (% w/w) |
| --- | --- |
| Oxycodone | 26 |
| Corn Oil | 49 |
| Sucrose acetate isobutyrate | 2 |
| Bentonite | 1 |
| Hydroxypropylmethyl cellulose (METHOCEL ™ K100M Premium) | 22 |

The samples were prepared:
1. Weigh Sucrose acetate isobutyrate and place in a glass beaker. Place beaker on a hot plate and heat until the Sucrose acetate isobutyrate becomes molten. Immerse Silverson high shear mixer fitted with a homogenizing head into the molten liquid and gradually add the oil under high shear.
2. Gradually add bentonite, and hydroxypropylmethyl cellulose while stirring vigorously until a homogeneous blend is observed.
3. Add oxycodone gradually while stirring vigorously until a homogeneous blend is observed.
4. The result is a semi-solid or paste which can be filled into hard gelatin capsules without "stringing".
5. Take samples from top, middle and bottom to determine potency and homogeneity of the mix.
6. Fill into hard gelatin capsules.

Example 4

Extended Release Oxycodone (Abuse Prevention Capsules)

| Component | Amount (% w/w) |
| --- | --- |
| Oxycodone | 26 |
| Cotton seed oil | 45 |
| Carbopol 934 | 5 |
| Bees Wax | 3 |
| Bentonite | 1 |
| Hydroxypropylmethyl cellulose (METHOCEL ™ K100M Premium) | 20 |

The samples were prepared:
1. Weigh Bees Wax and place in a glass beaker. Place beaker on a hot plate and heat until the Bees Wax becomes molten. Immerse Silverson high shear mixer fitted with a homogenizing head into the molten liquid and gradually add the oil under high shear.
2. Gradually add bentonite, carbopol and hydroxypropylmethyl cellulose while stirring vigorously until a homogeneous blend is observed.
3. Add oxycodone gradually while stirring vigorously until a homogeneous blend is observed.
4. The result is a semi-solid or paste which can be filled into hard gelatin capsules without "stringing".
5. Take samples from top, middle and bottom to determine potency and homogeneity of the mix.
6. Fill into hard gelatin capsules.

Example 6

Extended Release Oxycodone (Abuse Prevention Capsules)

| Component | Amount (% w/w) |
| --- | --- |
| Oxycodone | 26 |
| Castor oil | 45 |
| Carbopol 934 | 5.5 |
| Polyethylene Glycol 8000 | 5 |
| Bentonite | 2.5 |
| Polyethylene Oxide WSR-303 | 16 |

The samples were prepared:

1. Weigh polyethylene glycol and place in a glass beaker. Place beaker on a hot plate and heat until the polyethylene glycol becomes molten. Immerse Silverson high shear mixer fitted with a homogenizing head into the molten liquid and gradually add the oil under high shear.
2. Gradually add bentonite, carbopol and polyethylene oxide while stirring vigorously until a homogeneous blend is observed.
3. Add oxycodone gradually while stirring vigorously until a homogeneous blend is observed.
4. The result is a semi-solid or paste which can be filled into hard gelatin capsules without "stringing".
5. Take samples from top, middle and bottom to determine potency and homogeneity of the mix.
6. Fill into hard gelatin capsules.

Example 6

Extended Release Oxycodone (Abuse Prevention Capsules)

| Component | Amount (% w/w) |
| --- | --- |
| Oxycodone | 25 |
| Corn oil | 40 |
| Carbopol 934 | 8 |
| Sodium lauryl sulphate | 10 |
| Hydroxypropylmethyl cellulose (METHOCEL™ K100M Premium) | 18 |

The samples were prepared:

1. Weigh the oil in a glass beaker. Immerse Silverson high shear mixer fitted with a homogenizing head into the oil.
2. Gradually add carbopol and hydroxypropylmethyl cellulose while stirring vigorously until a homogeneous blend is observed.
3. Add oxycodone gradually while stirring vigorously until a homogeneous blend is observed.
4. The result is a semi-solid or paste which can be filled into hard gelatin capsules without "stringing".
5. Take samples from top, middle and bottom to determine potency and homogeneity of the mix.
6. Fill into hard gelatin capsules.

Example 7

Combination Extended Release Oxycodone+Immediate Release Tramadol (Abuse Prevention Capsules)

(i) Preparation of immediate release tramadol paste (Preparation 1)

| Component | Amount (% w/w) |
| --- | --- |
| Tramadol | 25 |
| Corn oil | 40 |
| Starch 1500 | 8 |
| Crospovidone | 5 |
| Hydroxypropylmethyl cellulose (METHOCEL™ E5 Premium LV) | 18 |

(ii) Preparation of controlled release Oxycodone paste (Preparation 2) This is made as taught in Example 1.

(iii) Preparation of combination Extended release Oxycodone+Immediate release Tramadol (Abuse prevention capsules).

Fill the required amount of preparation 1 into the hard gelatin capsule followed by preparation 2. Seal the capsule. In another embodiment a separation layer made of a wax such as carnuba wax or a high molecular weight polyethylene glycol e.g., PEG 8000 may be filled into the capsule to separate two or more preparations where incompatibility or cross migration of components is of concern. In this way several combinations of active substances are possible.

Example 8

Film Coated Abuse Prevention Capsules

This comprises film coating capsules made in Example 1 with a polymethacrylate such as Eudragit L or S to impart a delayed or timed release characteristics or lag phase.

Example 9

Film Coated Abuse Prevention Capsules

This comprises film coating capsules made in Example 1 with a cellulose ether such as ethylcellulose alone or in combination with water soluble polymers e.g., hydroxypropylmethyl cellulose.

Example 10

Film Coated Abuse Prevention Capsules

This comprises film coating capsules made in Example 1 with a polymethacrylate such as Eudragit E to provide a protective sealing coat or moisture barrier or improve mechanical properties.

The invention claimed is:

1. A dosage form dispensing device comprising a pharmaceutical composition, the pharmaceutical composition comprising:
   i) an addictive opioid agonist, narcotic analgesic, barbiturate, central nervous system stimulant, and/or tranquilizer;
   ii) an oily substance, a waxy substance, a fatty substance, or a combination thereof;
      wherein the oily substance is selected from the group consisting of apricot kernel oil, avocado oil, black currant oil, y-linolenic acid (GLA), borage oil, canola oil, carrot oil, castor oil, coconut oil, corn oil, cottonseed oil, evening primrose oil, flaxseed oil, a-linolenic acid (ALA), grapeseed oil, hazelnut oil, hemp oil, jojoba oil, golden jojoba oil, water-white kukui nut oil, macadamia nut oil, oat oil, olive oil, extra virgin olive oil, palm oil, parsley seed oil, peach kernel oil, peanut oil, pecan oil, pistachio oil, pumpkinseed oil, rice bran oil, rose hip seed oil, rosemary oil, safflower oil, linoleic safflower oil, sesame oil, sesame oil toasted, soybean oil, sunflower oil, salad sunflower oil, vegetable oil, glycerine, walnut oil, wheat germ oil, mineral oil, and combinations thereof;

wherein the waxy substance is selected from the group consisting of carnauba wax, candelilla wax, bayberry wax, auricurry wax, espalt wax, bees wax, breached bees wax, insect wax, spermaceti, shellac, lanolin, white beeswax, yellow beeswax, paraffin, petrolatum, microcrystalline wax, and combinations thereof; and wherein the fatty substance is selected from the group consisting of caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, and combinations thereof;

iii) a clay;
iv) a controlled release agent;
v) an aqueous vehicle; and
vi) an emulsifier;

wherein the oily, waxy, fatty substance, or combination thereof is in an amount sufficient to dissolve, disperse, emulsify, or suspend the addictive opioid agonist, narcotic analgesic, barbiturate, central nervous system stimulant, and/or tranquilizer, the clay, and the controlled release agent to form the composition, wherein the composition is a homogeneous semisolid; and wherein the dosage form dispensing device is configured for oral, vaginal, anal, ocular, buccal, or transdermal application.

2. The dosage form dispensing device of claim 1, further comprising a disintegrant.

3. The dosage form dispensing device of claim 1, wherein the clay is bentonite, montmorillonite, pascalite, smectite, illite, sepiolite, palygorskite, muscovite, allevardite, amesite, hectorite, fluorohectorite, saponite, beidellite, talc, nontronite, stevensite, mica, vermiculite, fluorovermiculite, halloysite, fluorine-containing synthetic types of mica, phyllosilicates, beidellite, volkonskoite, hectorite, sauconite, sobockite, svinfordite, mixed illite/smectite minerals, wherein the illite/smectite minerals are selected from the group consisting of: rectorite, tarosovite, ledikite, or admixtures of illites with the clay minerals named above.

4. The dosage form dispensing device of claim 1, further comprising a nasal irritant.

5. The dosage form dispensing device of claim 1, wherein the dosage form dispensing device is a transdermal patch.

6. The dosage form dispensing device of claim 1, wherein the dosage form dispensing device is a capsule.

7. The dosage form dispensing device of claim 6, wherein the capsule is a hard gelatin capsule or a soft gelatin capsule.

8. The dosage form dispensing device of claim 6, which is coated with a film coat comprising cellulose esters or polymethacrylates or polyethylene glycol or cellulose ethers, esters or a combination thereof.

9. The dosage form dispensing device of claim 1, further comprising an excipient selected from solubilizing agents, emulsifying agents, suspending agents, fillers, compression agents, stabilizers, pH altering agents, buffers, lubricants, and glidants.

10. A dosage form dispensing device comprising a pharmaceutical composition, the pharmaceutical composition comprising:

i) an addictive opioid agonist, narcotic analgesic, barbiturate, central nervous system stimulant, and/or tranquilizer;

ii) an oily substance, a waxy substance, a fatty substance, or a combination thereof wherein the oily substance is selected from the group consisting of apricot kernel oil, avocado oil, black currant oil, y-linolenic acid (GLA), borage oil, canola oil, carrot oil, castor oil, coconut oil, corn oil, cottonseed oil, evening primrose oil, flaxseed oil, a-linolenic acid (ALA), grapeseed oil, hazelnut oil, hemp oil, jojoba oil, golden jojoba oil, water-white kukui nut oil, macadamia nut oil, oat oil, olive oil, extra virgin olive oil, palm oil, parsley seed oil, peach kernel oil, peanut oil, pecan oil, pistachio oil, pumpkinseed oil, rice bran oil, rose hip seed oil, rosemary oil, safflower oil, linoleic safflower oil, sesame oil, sesame oil toasted, soybean oil, sunflower oil, salad sunflower oil, vegetable oil, glycerine, walnut oil, wheat germ oil, mineral oil, and combinations thereof;

wherein the waxy substance is selected from the group consisting of carnauba wax, candelilla wax, bayberry wax, auricurry wax, espalt wax, bees wax, breached bees wax, insect wax, spermaceti, shellac, lanolin, white beeswax, yellow beeswax, paraffin, petrolatum, microcrystalline wax, and combinations thereof; and wherein the fatty substance is selected from the group consisting of caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, corianyl alcohol, ceryl alcohol, myricyl alcohol, and combinations thereof;

iii) a clay; and
iv) a controlled release agent;

wherein the oily, waxy, fatty substance, or combination thereof is in an amount sufficient to dissolve, disperse, emulsify, or suspend the addictive opioid agonist, narcotic analgesic, barbiturate, central nervous system stimulant, and/or tranquilizer, the clay, and the controlled release agent to form the composition, wherein the composition is a homogeneous semisolid;

wherein the dosage form dispensing device is configured for oral, vaginal, anal, ocular, buccal, or transdermal application;

wherein the dosage form dispensing device is a capsule; and wherein the capsule comprises two different semisolid compositions, a first semisolid composition comprising the addictive opioid agonist, narcotic analgesic, barbiturate, central nervous system stimulant, and/or tranquilizer and a second semisolid composition comprising the same or different addictive opioid agonist, narcotic analgesic, barbiturate, central nervous system stimulant, and/or tranquilizer.

11. The dosage form dispensing device of claim 10, wherein the capsule further comprises a separation layer for separating the first semisolid composition and the second semisolid composition.

12. The dosage form dispensing device of claim 11, wherein the separation layer is made of carnauba wax or a high molecular weight polyethylene glycol.

* * * * *